(12) United States Patent
Ramakrishnan et al.

(10) Patent No.: US 6,953,874 B2
(45) Date of Patent: Oct. 11, 2005

(54) TRANSGENIC ANIMALS HAVING A MODIFIED GLYCOPROTEIN V GENE

(75) Inventors: Vanitha Ramakrishnan, Belmont, CA (US); David R. Phillips, San Mateo, CA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/775,803

(22) Filed: Feb. 5, 2001

(65) Prior Publication Data

US 2003/0167487 A1 Sep. 4, 2003

Related U.S. Application Data

(63) Continuation of application No. PCT/US99/17594, filed on Aug. 4, 1999.
(60) Provisional application No. 60/109,797, filed on Aug. 4, 1998.

(51) Int. Cl.[7] .............................................. G01N 33/00
(52) U.S. Cl. ................................ 800/3; 800/9; 800/18; 800/21; 800/25; 435/325; 435/354; 435/355
(58) Field of Search ........................... 800/3, 9, 18, 21, 800/23–25, 4, 5, 8, 13, 14; 435/325, 354, 355; 424/9.2, 93.2

(56) References Cited

U.S. PATENT DOCUMENTS

5,413,923 A    5/1995    Kucherlapati et al. ..... 435/172.3

FOREIGN PATENT DOCUMENTS

WO    WO 99/53032    10/1999    ............. C12N/5/10

OTHER PUBLICATIONS

Moreadith et al., J. Mol. Med. 75:208–216, 1997.*
Ravanat et al., Blood. ;89:3253–62, 1997.*
Ngo et al., The Protein Folding Problem and Tertiary Structure Prediction, Birkhauser Boston, 1994, pp. 491–494.*
Chiu et al., Folding and Design, 1998, pp. 223–228.*
L–M Houdebine, Journal of Biotechnology, "Production of pharmaceutical proteins from transgenic animals," 1994, 34,pp. 269–287.*
RM Strojek et al., Genetic Engineering:Principles and methods, " The use of transgenic animal techniques for livestock improvement," 1988, vol. 10, pp. 221–246.*
LJ Mullins et al., Perspectives Series: Molecular Medicine in Genetically Engineered Animals,"Transgenesis in the Rat and Larger Mammals," Apr. 1996, vol. 97, No. 7, pp. 1557–1560.*

RJ Wall, Theriogenology, "Transgenic Livestock: Progress and Prospects for the Future," 1996, 45:57–68.*
T Rulicke et al.,Experimental Physiology, "Special Review Series–Gene Manipulation and Integrative Physiology, "2000,85.6,pp. 589–601.*
JO Bishop, Reprod Nutr Dev., "Chromosomal insertion of foreign DNA," 1996,36,pp. 607–618.*
IA Polejaeva et al., Theriogenology, "New Advances in Somatic Cell Nuclear Transfer: Application in Transgenesis," 2000, 53: pp. 117–126.*
CD Sigmund, Arterioscler Thromb Vasc Biol., "Viewpoint: Are Studies in Genetically Altered Mice Out of Control?," 2000;20:1425–1429.*
D Humpherys et al., Science, "Epigenetic Instability in ES Cells and Cloned Mice," Jul.2001, vol. 293, pp. 95–97.*
S Moog et al., Hemostasis, Thrombosis and Vascular Biology,"Platelet glycoprotein V binds to collagen and participates in platelet adhesion and aggregation," Aug. 2001, vol. 98, No. 4, pp. 1038–1046.*
ML Kahn et al., Hemostasis, Thrombosis, and Vascular Biology, "Glycoprotein V–Deficient Platelets have undiminished Thrombin Responsiveness and Do not Exhibit a Bernard–Soulier Phenotype," Dec. 1999, vol. 94, No. 12, pp. 4112–4121.*
Dong et al., (1997) Role of Glycoprotein V in the Formation of the Platelet High–Affinity Thrombin– Binding Site, Blood 89, 4355–4363.
Law et al., (1999) Signal Transduction Pathways for Mouse Platelet Membrane Adhesion Receptors, Thrombosis & Haemostasis 82, 345–352.
Ramakrishnan et al., (1999) Increased Thrombin Responsiveness in Platelets From Mice Lacking Glycoprotein V, Proceedings of the National Academy of Sciences of USA 96, 13336–13341.
Ramakrishnan et al., (1998) Targeted Deletion of the GPV Gene in Mice: A Model For Studying the Functional Role of GPV in Mouse Platelets, Blood 92, suppl. 1, abstract #1434.

* cited by examiner

*Primary Examiner*—Scott D. Priebe
*Assistant Examiner*—Brian Whiteman
(74) *Attorney, Agent, or Firm*—Millennium Pharmaceuticals, Inc.

(57) ABSTRACT

The present invention relates to nonhuman transgenic animals in which the GP V gene has been modified. The invention is also useful for identifying agents that modulate the biological functions of GP V, including the screening and identification of potential therapeutic agents.

11 Claims, 13 Drawing Sheets

FIG. 1A

```
GAATTCATTG GCCTTATTTA AGAAATAAAA TGTTGAGCAA AAGAGATGGC        50
TCATCAGTA AAGATACCTC CCAAGACATG GTGTGAGTCC TTGGAACCT        100
ACGTGGAGGA AGGTGAGAAC CAATTGCCTA AAGTTTTCTG ACACCCACAA       150
GTGAGGCACT GCCACATGCA CCCACATACT CCTGCACAGG AATGAGTTAG       200
TGCAATGTAG CATGGAAAAA AACCAAAAGT GTGGCCCATG TAATGACAGC       250
CTGCTATTTC TGGGAAAACT TAGGCCCTCT ACTCTCTAGC TTTTACAAAA       300
GGACTTTTAA CTATGGACTC TGAAAGTTTG AAAGCTCTTG TCATTAAAAAC      350
CTAGAATATG CCCTATGGAG ATAGTCTTTT TCTTGACTTT TTATCTGGTA       400
AGGTCTTTAT CTTGAGGATG CAAGAATACT TCCCTCTTCC TCTCTGAAGT       450
GCCAAGTCAC AAGCAGAGCT GCAAGCCTTT CAGTCAGTCC AGGGTGCAGA       500
ACTGCTTCAG GTAAGGCCAA ATATTCTTAA ATTAGTGTAT GCAGTTAGAG       550
GCTCAGTCTG TATAGGGGCA GAAGGAGACC TGGTACAAGA AACAGTACAA       600
ATTTTTACTT GGGAAACAGA GTAAACTAGT ATTACTGTGT GCTTCCTGGG       650
TAACTCAATG CCCAGAGTAG TTTTATTAAG CAGCTTGGTG TATAAGCAAA       700
CAGTAGCTCA TTATTAAAT GTGTGAGTCA GAAAAACATC TTCAAATGCT        750
ACTTATGTGA CACTTAAATT AACCTCATGT ACACTGGAGC GACCAGCCTA       800
CTGCACTCGT GTTACTGTAA CAGTGCAAAG TTCAGAAAAG CATGGCATAA       850
AGCAATGGGC ATTATCACCT GCACCACTGG GCTCCGGGCC GGGAGTTACA       900
AAACGGTGTA ATGAGTTGTG GGGTGTTGGT ACTTTGAAAA TATGTAAGAA       950
ATTGAATCTA GTGGAAGTGG GCCTTGCTGC GGTTCTCTTG CTGACTGTTG      1000
GGGATAAAGC TCCCTGCTTA ACTTGTTAAA GTCAGTGACA CAGCCAGTCC      1050
CAGGAGGCGT TGCTTTCTAT TCTCTGAAAA AGACCGTAGC AATTTAATT       1100
CGTTCTGTAA CGATTTTAAG GTATTCTGTA GCTTGAAAAT GCCCAAATGT      1150
CAATGCTCTA AACAGAACCG GGGAGATGGC TGACTGGATA AAAATGGGAA      1200
CCTGTAAGAC TGATCTACTC TCCAATACCC ACATATCCTG AATAGAAAAG      1250
TAATTTTTTT TTAATCAGCC TTTGTAAGAT AGAGGAAGAC TTGGTTGTAT      1300
CTGAGCGTTC CAAGGCCGTG AGAGTGCTGG CCCAAAACT GTGCTTGCAG       1350
CAGTGCGTGC AGGGCTCCAG GATATGCTCT GAGCCTTGTT TTTGCTCTTG     1400
CATTTCAGAC
```

FIG. 1B

```
                   (start)
TGCGTGCCCA  ATGCTAAGAA  GCGCCCTGCT  GTCCGCGGTG  CTCGCACTCT    1450
GATGCCGCGC  ACCTTTTCCC  TGCCCAAAAA  CCTGCAAGTG  TGTGGTCCGC    1500
TCTGCCTACG  AGTGCTCGGG  CGGCAGCGTG  GCTCACATCG  CTGAGCTAGG    1550
AACCTCACAC  AACCTCACAC  ACATCCTGCT  CTTCCGAATG  GACCAGGGCA    1600
TATTGCGGAA  CCACAGCTTC  AGCGGCATGA  CAGTCCTTCA  GCGCCTGATG    1650
CTCTCAGATA  GCCACATTTC  CGCTTGACGA  CCCGGCACCT  TCAATGACCT    1700
GGTAAAACTG  AAAACCCTCA  GGTTGACGCG  CAACAAAATC  TCTCGTCTTC    1750
CACGTGCGAT  CCTGGATAAG  ATGGTACTCT  TGGAACAGCT  GTTCTTGGAC    1800
CACAATGCAC  TAAGGACCT   TGATCAAAAC  CTGTTTCAGC  AACTGCGTAA    1850
CCTTCAGGAG  CTCGGTTTGA  ACCAGAATCA  GCTCTCTTTT  CTTCCTGCTA    1900
ACCTTTTCTC  GAGCCTGAGA  GAACTGAAGT  TGTTGGATTT  ATCGCGAAAC    1950
AACCTGACCC  ACCTGCCCAA  GGGACTGCTT  TGTTGGATTT  TTAAGCTTGA    2000
GAAACTGCTG  CTCTATTCAA  ACCAGCTCAC  GTCTGTGGAT  TCGGGCTGC     2050
TGAGCAACCT  GGGCGCCCTG  ACTGAGCTGC  GGCTGGAGCG  GAATCACCTC    2100
CGCTCCGTAG  CCCCGGGTAG  CTTCGACCGC  CTCGGAAACC  TGAGCTCCTT    2150
GACTCTATCC  GAAACCTCC   TGGAGTCTCT  CCGGCCCGCG  CTCTTCCTTC    2200
ACGTGAGCAG  CGTGTCTCTG  CTGACTCTGT  TCGAGAACCC  CCTGAGGAG     2250
CTCCCGGACG  TGTTGTTCGG  GGAGATGGCC  GGCCTGCGGG  AGCTGTGGCT    2300
GAACGGCACC  CACCTGAGCA  CGCTGCCCGC  CGCTGCCCGC  CGCAACCTGA    2350
```

FIG. IC

```
GCGGCTTGCA GACGCTGGGG CTGACGCGGA ACCCGCGCCT GAGCGCGCTC  2400
CCGCGCGGCG TGTTCCAGGG CCTACGGGAG CTGCGCGTGC TCGCGCTGCA  2450
CACCAACGCC CTGGCGGAGC TGCGGGACGA CGCGCTGCGC GGCCTCGGGC  2500
ACCTGCGCCA GGTGTCGCTG CGCCACAACC GGCCACAAGC CCTGCCCCGC  2550
ACGCTCTTCC GCAACCTCAG CAGCCTCGAG AGCGTGCAGC TAGAGCACAA  2600
CCAGCTGGAG GCAGCTGCCA GAGACGTGTT CGCGGCTCTG CCCCAGCTGA  2650
CCCAGTCCT GCTGGGTCAC AACCCCTGGC TCTGCGACTG TGGCCTGTGG  2700
CCCTTCCTCC AGTGGCTGCG GCATCACCCG GACATCCTGG GCCGAGACGA  2750
GCCCCCGCAG TGCCGTGGCC CGGAGCCACG CGCCAGCCTG TCGTTCTGGG  2800
AGCTGCTGCA GGGTGACCCG TGGTGCCCGG ATCCTCGCAG CCTGCCTCTC  2850
GACCCTCCAA CCGAAAATGC TCTGGAAGCC CCGGTTCCGT CCTGGCTGCC  2900
TAACAGCTGG CAGTCCCAGA CGTGGGCCCA GCTGGTGGCC AGGGGTGAAA  2950
GTCCCAATAA CAGGCTCTAC TGGGGTCTTT ATATTCTGCT TCTAGTAGCC  3000
CAGGCCATCA TAGCCGCGTT CATCGTGTTT GCCATGATTA AAATCGGCCA  3050
GCTGTTTCGA ACATTAATCA GAGAGAAGCT CTTGTTAGAG GCAATGGGAA  3100
AATCGTG
   (stop)
        TAA CTAATGAAAC TGACCAGAGC ATTGTGGACG GGGCCCCAAG  3150
GAGAATGCAG TCAGGATGCT GGCGTGCCAT TACACTATTT CCCAGGCCTT  3200
TTCTCCTCTC CCGTGCTCTT AGTGTCTCTT CTTCTCCCCT CTCTTCAGAA  3250
GTAGCTTTTG TAAATCGCTA CTGCTTTCTA GCCTGGCCTG GGTTACCTCC  3300
TCTGCTGTTA GTTTCAAGGG GGCTGAGGGT GGGGGTTCGA CGGGACTTGG  3350
CTCATCAGGT CCAACTGTGC AGCGCTGGGT GCCTAGTGGA GAGAGGAGCC  3400
CTTTCTTGGT TTCTGAATTT GAGGACACAT CCTGCCAGTG GGCAAGACCT  3450
CTCCGGGACC CAGCAAGGGT TGAGTAACAT TTGCTGAAGG AACACCGGCT  3500
TAAAACGAAC CCTAGGTCCA AGAGATGAAG GCTCTTCCCA AAATAAAGGT  3550
GGAGTGTTCT TGTCCCTTTA CCTGAAAGGA GAATTC                 3586
```

FIG. 2

```
MLRSALLSAV LALLRAQPFP CPKTCKCVVR DAAQCSGGSV AHIAELGLPT
NLTHILLFRM DQGILRNHSF SGMTVLQRLM LSDSHISAID PGTFNDLVKL    50
KTLRLTRNKI SRLPRAILDK MVLLEQLFLD HNALRDLDQN LFQQLRNLQE   100
LGLNQNQLSF LPANLFSSLR ELKLLDLSRN NLTHLPKGLL GAQVKLEKLL   150
LYSNQLTSVD SGLLSNLGAL TELRLERNHL RSVAPGAFDR LGNLSSLTLS   200
GNLLESLPPA LFLHVSSVSR LTLFENPLEE LPDVLFGEMA GLRELWLNGT   250
HLSTLPAAAF RNLSGLQTLG LTRNPRLSAL PRGVFQGLRE LRVLALHTNA   300
LAELRDDALR GLGHLRQVSL RHNRLRALPR TLFRNLSSLE SVQLEHNQLE   350
TLPGDVFAAL PQLTQVLLGH NPWLCDCGLW PFLQWLRHHP DILGRDEPPQ   400
CRGPEPRASL SFWELLQGDP WCPDPRSLPL DPPTENALEA PVPSWLPNSW   450
QSQTWAQLVA RGESPNNRLY WGLYIYLLVA QAIIAAFIVF AMIKIGQLFR   500
TLIREKLLLE AMGKSC                                       550
                                                        566
```

FIG. 3A

```
5'-TGATCGGAAC TGAAAGACCT CCCGCGATAC CTGCCAGAGG CAGTGGCTCT    50
             TRE
TCCCTGTGGT CCAGGGCTGA CTGACTTTGA AGGTAATTTC AGTCAACCCA GCCTTTACTG   110
GGCTCTGACT GCATTAGGCT GCATCAAAGG GGATTGGATC CCATGATTCT TTATATCTTC   170
TGACATTAAG CCTTTGTCAG CTATAGGTGT TACAAATATC TTTAGTTTGT GGTTTATCTT   230
TTCCCCTTTT TTATGGTGTC TTGAAGGATA GAAGTCTTAA TGCAGACAGC ATTATCAGTG   290
TGTTCAAAAG ACAGCTAGAC ACGTTTTGCC TATAGACAAA TGGGCAAAAG GAAACCCAGC   350
TTTCTCAAAT GAAGCACAAG TGGGCCTTAA TTATGTGAAA AGGTGTTCAA GTTCATCATT   410
AAACAGGGAA AGGAAAAGTT AAAACCATGC TGAGATATCT TTCATAGAAA TGGCAAAAAG   470
     Ets-1                              Ets-1
CAGGAAGTGC CACGTGTGGG CAGAGAGGAA GGACAGGAAC TCTCACAAAT GGCAGGTGTC   530
ATCGTAGACC AACACAACCA CTTTGGAGAG CAGTTTGACT TTCCCCAGTT AAACTGAACA   590
TGTGAGCGGC CGGGCGTGGT GGCTCATGCC TGTAATCCCA GCAGTTTGGG AGGCCGAGGC   650
GGGCGGATTG CCTGAGCTCA GGAGTTCAAG ACCAGCCAGG GCAACACGGT AAAACCCCGT   710
CTCTACTAAA ATACAAAAAA TTAGCTGGGC GTGATGGTGT GTGCCTGTAA TCCCAGCTAC   770
TTGTGAGGCC GAGGCAGGAG AATTGCTTGA ACCAGGGAGC AGGAGGTTGC AGTGAGCCGA   830
GATCGCACCA CTGCACCCCA GCCTGGCGAC AGAGTCCCCC TCCCCACCA AAAAAACAAC   890
     Ets-1
AAGTGAGCAT CCTGCAACCT AGCAATGCCA TTGTTGAACA AGTTCAAAGA TGTTCTTAGC   950
CTTATTAGTC CCAAAAGGAA GAAAAAAATG GAGGATTTGA GAATGTTCTT AGCTTTATTG  1010
CTAAGCGGAG AAAGAAAAAC AACACATACC AAAAAAAAAA AAAAAAAAAA AAAAAAACAA  1070
AAAACCTGGG TGGGAAATTA GGGCCATGTG GCATGAAAAG GAAGACCCAG GGGAAGTGTG  1130
             Sp1                                       Ets-1
GCCCATCTAG GGGTGTGGGT ACTGCAGTGA TCCAGCTGTA TCACTGAACT TCCGTGGCAT  1190
           TATA
CATAGAGTTA TATTGTGCCA TTTATGGAAA AACTCTCCCC ACTGCTCTTG GCTTTGACAG  1250
            TATA                  GATA
TAGGAATCAG GTTATATATG GTCTCTCGGT TTGAAGATAT TTGTCATTAA AAACCAGAAC  1310
      GATA                                            Ets-1
AAGGGCTCTG AGATAGGGTC CTTTCCTGAC CTACTCTGGT AAAGTCTTTA TCCTCAGGAT  1370
GCAAGGATAC CACCCTCTTC CTGTGGAAAG TGTCGAATCA CATGCAGAGC TCTAAGTCTT  1430
▽
TCAGTTACTT TGGAGTGCAG AACCATTTCA Ggtaaggcca aatatttaa acattagtat  1490
agggaattag agggctcttt agtctgtgtg tgcatgagaa gtaaaattgc acgagaagca  1550
atttatgtaa aatttcgctt aggaaacatt gtttttgglag gttagtagta tggtgtgtat  1610
ttcccagaaa attcagtgcc gtgagtatta cctttagtta agcatcttag aaatagtagc  1670
tcttatigtt tatggctaag tcagaaatac tacccteaaa ttctatgtga ccctagttat  1730
actgttgagc ctttctgtgc ctctgtcct tcatcettga atcgggata atataettac  1790
ctcctaaggt tattgtaagg attaaatgca tgtagtataa ataaagagct gagaacaatg  1850
catggcgtaa agtgataggt attattatat gtttttgttg gctgttgatt gaagggtgttt  1910
gctgtttgg gggtgtcctt taatagagta acttggtact gtggaaatag catgattgtg  1970
agcaaaagaa tcagatgggtg gtggctgcag acttttgctgt tcccttcttg actgttggtt  2030
atagccaatg caggggtaagt tataaagtca agagcagagc cgtttcaca atggacattg  2090
cttgtgatg tctgtgagct tgaatgtgag aatgattatt ttaatctct atgtaaagac  2150
tttaaagtat tggctattcg gtagcttgat ttctctgtaa tctcatgctt taaactgaga  2210
gtgggaaatc aataaagcaa aagcatgagg ccacgcagtg tagaatgagt gtcttttcac  2270
cacgtagggga aatctgtagt cctaagaaaa gagggagtga gaattctggc gaaaagattg  2330
tgcctctgca caaagtgcag gatcccaggg ttcagtacag gcgcgaacgc tcctgtgtgt  2390
                                          Met
tgaccacact cccacggttg ctttttagA C ATG CTGAGG GGGACTCTAC TGTCCGCGGT  2450
```

FIG. 3B

```
GCTCGGGCTT CTGCGCGCCC AGCCCTTCCC CTGTCCGCCA GCTTCCAAGT GTGTCTTCCG 2510
GGACGCCGCG CAGTGCTCGG GGGCGACGT GGCGCGCATC TCCGCGCTGG GCCTGCCCAC 2570
CAACCTCACG CACATCCTGC TCTTCGGAAT GGGCCGCGGC GTCCTGCAGA GCCAGAGCTT 2630
CAGCGGCATG ACCGTCCTGC AGCGCCTCAT GATCTCCGAC AGCCACATTT CCGCCGTTGC 2690
CCCCGGCACC TTCAGTGACC TGATAAAACT GAAAACCCTG AGGCTGTCGC GCAACAAAAT 2750
CACGCATCTT CCAGGTGCGC TGCTGGATAA GATGGTGCTC CTGGAGCAGT TGTTTTTGGA 2810
CCACAATGCG CTAAGGGCA TTGACCAAAA CATGTTTCAG AAACTGGTTA ACCTGCAGGA 2870
GCTCGCTCTG AACCAGAATC AGCTCGATTT CCTTCCTCCC AGTCTCTTCA CGAATCTGGA 2930
GAACCTGAAG TTGTTGGATT TATCGGGAAA CAACCTGACC CACCTGCCCA AGGGGTTGCT 2990
TGGAGCACAG GCTAAGCTCG AGAGACTTCT GCTCCACTCG AACCGCCTTG TGTCTCTGGA 3050
TTCGGGGCTG TTGAACAGCC TGGGCGCCCT GACGGAGCTG CAGTTCCACC GAAATCACAT 3110
CCGTTCCATC GCACCCGGGG CCTTCGACCG GCTCCCAAAC CTCAGTTCTT TGACGCTTTC 3170
GAGAAACCAC CTTGCGTTTC TCCCTCTGC GCTCTTTCTT CATTCGCACA ATCTGACTCT 3230
GTTGACTCTG TTCGAGAACC CGCTGGCAGA GCTCCCGGGG GTGCTCTTCG GGAGATGGG 3290
GGGCCTGCAG GAGCTGTGGC TGAACCGCAC CCAGCTGCGC ACCCTGCCCG CCGCCGCCTT 3350
CCGCAACCTG AGCCGCCTGC GGTACTTAGG GGTGACTCTG AGCCCGCGGC TGAGCGCGCT 3410
TCCGCAGGGC GCCTTCCAGG GCCTTGGCGA GCTCCAGGTG CTCGCCCTGC ACTCCAACGG 3470
CCTGACCGCC CTCCCCGACG GCTTGCTGCG CGGCCTCGGC AAGCTGCGCC AGGTGTCCCT 3530
GCGCCGCAAC AGGCTGCGCG CCCTGCCCCG TGCCCTCTTC CGCAATCTCA GCAGCCTGGA 3590
GAGCGTCCAG CTCGACCACA ACCAGCTGGA GACCCTGCCT GGCGACGTGT TTGGGGCTCT 3650
GCCCCGGCTC ACGGAGGTCC TGTTGGCGCA CAACTCCTGG CGCTGCGACT GTGGCCTGGG 3710
GCCCTTCCTG GGGTGGCTGC GGCAGCACCT AGGCCTCGTG GGCGGGGAAG AGCCCCCACG 3770
GTGCGCAGGC CCTGGGGCGC ACGCCGGCCT GCCGCTCTGG GCCCTGCCGG GGGGTGACGC 3830
CGAGTGCCCG GGCCCCCGGG GCCCGCCTCC CCGCCCCGCT GCCCACACCT CCTCGGAAGD 3890
CCCTGTCCAC CCAGCCTTGG CTCCCAACAG CTCAGAACCC TGGGTGTGGG CCCAGCCGGT 3950
GACCACGGGC AAAGGTCAAG ATCATAGTCC GTTCTGGGGG TTTTATTTTC TGCTTTTAGC 4010
TGTTCAGGCC ATGATCACCG TGATCATCGT GTTTGCTATG ATTAAAATTC GCCAACTCTT 4070
                                    STOP
TCGAAAATTA ATCAGAGAGA GAGCCCTTGG GTAACCAAT GGGAAAATCT TCTAATTACT 4130
TAGAACCTGA CCAGATGTGG CTCGGAGGGC AATCCAGACC CGCTGCTGTC TTGCTCTCCC 4190
TCCCCTCCCC ACTCCTCCTC TCTTCTTCCT CTTCTCTCTC ACTGCCACGC CTTCCTTTCC 4250
CTCCTCCTCC CCCTCTCCGC TCTGTGCTCT TCATTCTCAC GGGCCCGCAA CCCCTCCTCT 4310
CTCTGTCCCC GCCCGTCTCT GGAAACTGAG CTTGACGTTT GTAAACTGTG GTTGCCTGCC 4370
TTCCCAGCTC CACGCGGTGT GCGCTGACAC TGCCGGGGGG CTGGACTGTG TTGGACCCAT 4430
CCTTGCCCCG CTGTGCCTGG CTTCGCCTCT GGTGGAGAGA GGGACCTCTT CAGTGTCTAC 4490
TGAGTAAGGG GACAGCTCCA GGCCGGGGCT GTCTCCTGCA CAGAGTAAGC CGGTAAATGT 4550
TTGTCAAATC AATGCGTGGA TAAAGGAACA CATGCCATCC AAGTGATGAT GGCTTTTCCT 4610
GGAGGGAAAG GATAGGCTGT TGCTCTATCT AATTTTTTGT TTTTGTTTTT GGACAGTCTA 4670
GCTCTGTGGC CCAGGCTGGC GTGCACTGGG CCGTCTCAGT TCACTGCACC CTCCGCCCTC 4730
CAGGTCAAG TGATTCTCAT GCCTCAGCGT TCTGAGTAGC TGGGATTAGA GGCGTGTGCC 4790
ACTACACCCG GCTAATTTTT GTACTTTTTA AAGTAGAGAC GGGCTTTGCC ATATTGGCCT 4850
GGCTGATCTC AAACTCCTGG TCTTGAACTC CTGGCCACAA GTGATCTGCC CGCCTTAGCC 4910
TCCCAAAGTG CTGGGATTAC AGGCGCAAGC CACTACACCT GCCCTCTTCA TCGAATTTTA 4970
TTTGAGAAGT AGAGCTCTTG CCATTTTTTC CCTTGCTCCA TTTTTCTCAC TTTATGTCTC 5030
TCTGACCTAT GGGCTACTTG GGAGAGCACT GGACTCCATT CATGCATGAG CATTTTCAGG 5090
ATAAGCGACT TCTGTGAGGC TGAGAGAGGA AGAAAACACG GAGCCTTCCC TCCAGGTGCC 5150
CAGTGTAGGT CCAGCGTGTT TCCTGAGCCT CCTGTGACTT TCCACTTGCT TTACATCCAT 5210
GCAACATGTC ATTTTGAAAC TCGATTGATT TGCATTTCCT GGAACTCTGC CACCTCATTT 5270
CACAAGCATT TATGGAGCAG TTAACATGTG ACTGGTATTC ATGAATATAA TGATAAGCTT 5330
```

FIG. 3C

```
GATTCTAGTT CAGCTGCTGT CACAGTCTCA TTTGTTCTTC CAACTGAAAG CCGTAAAACC 5390
TTTGTTGCTT TAATTGAATG TCTGTGCTTA TGAGAGGCAG TGGTTAAAAC ATTTTCTGGC 5450
GAGTTGACAA CTGTGGGTTC AAATCCCAGC TCTACCACTT ACTAACTGCA TGGGACTTTG 5510
GGTAAGACAC CTGCTTACAT TCTCTAAGCC TTCGTTTCCT GAACCTTAAA ACAGGATAAC 5570
ATAGTACCTG CTTCATAGAG TTTTGTGAGA ATTAAAGGCA ATAAAGCATA TAATGACTTA 5630
GCCCAGCGGC CTGCAGACAA TACATGTTAA TGAATGTTAG CTATTATTAC TAAAGATGAG 5690
CAATTATTAT TGCATCATG ATTTCTAAAG AAGAGCTTTG AGTTGGTATT TTTCTCTGTG 5750
TATAAGGGTA AGTCCGAACT TTGTCATACT GGAGGTTACA TTCACATCAG TCTGTCTTCC 5810
CCTGCGGATG GCCTCAGCCC TGGGTGGCCA GGCTCTGTGC TCACAGTCCA GAGCAATGGA 5870
TCCTCCAACA CCACCAGGTG GATGTGGAGC AGGAGAGCTG GATCGTGGCA TTTGTTTCTG 5930
GGTTCTGCAG TTGGGAGTTG GTTTCTGGGT TCTCCATTGG TCTACTTGTC TAGTCCCATA 5990
CCAGACTCAC GGTCTCCATT ATTGGAGCTT TAATAATTTT TGGTATAGGG TCATCTCTCC 6050
ACCTTGTTTT TCTTCTATTC TTGGTTCTTT GCAATTCTAT GAATATTTCA GGGTCAGCAT 6110
GTCAACTCCA TTGAAAAACC CTGCTGGGAT TTTAATAGAA CTTACAGCTC ACGCCTGTAA 6170
TCCCAGCACT TTGGGAGGCT GAGGTGGGTG GATCACAGGT CAGGAGTTTG AGAACAGCTG 6230
GCCAAGATGG TGAAACCCCG TCTCTACTAA AAATACAAAA ATTAGCTGGG TGCGGTGGCA 6290
GGTGCCTGTA GTCCCAGCTA CTTGGGACAC CGAGGCAGGA GAATCACTTG AACCCGGGAG 6350
GCGGAGGTTG CAGTGAGCCG AGATCGTGCC ACTGCACTCT AGCCTGGGCG ACAGAGCGAG 6410
ACTCCATCTC AAAAAAAAAG AAAAAGAAAA TTGCAGTAAA TTTAAAACTA ATTTGGGGAA 6470
GAATCTGTAT TTTTACAATA CCTAGTGTTC TTGCCAGTAA GCATGGTTCA TCTTCCCATT 6530
TATTTACGTC ATTTTAAATC TTTCAGTGAT GTTTAGAAT TTTTTTTATA AAAACCTTCA 6590
CTATAAGAAC AGAAAACCAA ACACCGCATG TTCTCACTCA TAGGTGGGAA TTGAACAATG 6650
AGAACACTTG GACACAGGGC GGGGAACGTC ACACGCCTGG ACTGTTGGGG GGTGGCTGG 6710
GAGAGGGATA GTGTTAGGAG AAATACCTAA TGTAAATGAC GAGTTAATGG TGCAGCCAAC 6770
CAACCTGGCA CATGTATTCA TATGTAACAA ACCTGCACGT TGTGCACATG TACCCTAGAA 6830
CTTAAAGTAT ATTAAAAAAA GAAACCTTGG CACTGATTTT GTTAGATTTA TTCCTACGTA 6890
TCCTTCCTCT TTTTTGATTT GTCATTGCTA TTGTAGATGG CATCTTTTTA AAAAGTTATA 6950
TTTTCTAAAG CAAAAAATAA AAAAAGTTGT ATTTCTAATT TTTATTACCA ATATATAAGA 7010
ATGTAATTTA TTTTTACATA ATTATCTTAT GTCTAGTAAT AATTCTGATA ATTTGCTTCT 7070
TCCTATTAAA ACCTTACACC CATTATTGAT TTATTTTTCT GTTTTAAAAT ATCTTCCTGC 7130
ACTGGCTAAA ACCTCCACTA TAATGTTGAG CAGAACAGTG AGGCATCCTT AGAACTATCT 7190
TGGTTGCAAA GGGTAGGTCT CTAATGTTTC ATCAATAAAT GTGATGTTTC TAGTCTGAGT 7250
TTGCTAAGTA TATTTTAAAA TAATCAGTAA AGTTAGATTT TATCCATTTT TATCTTAACT 7310
ATTGAGATGC TCATATCATT TTTCTTCTTC AATGTGTTAA AATGGTCAAT AAATTTATAG 7370
ATTTTGGAAA AGTAAATTCA TTCTTGCATT CCCGAAGTAA ACCAAGCCAT GCTATGTGTA 7430
TTTAAAATAT ATTGCTGAAT TC-3                                       7452
```

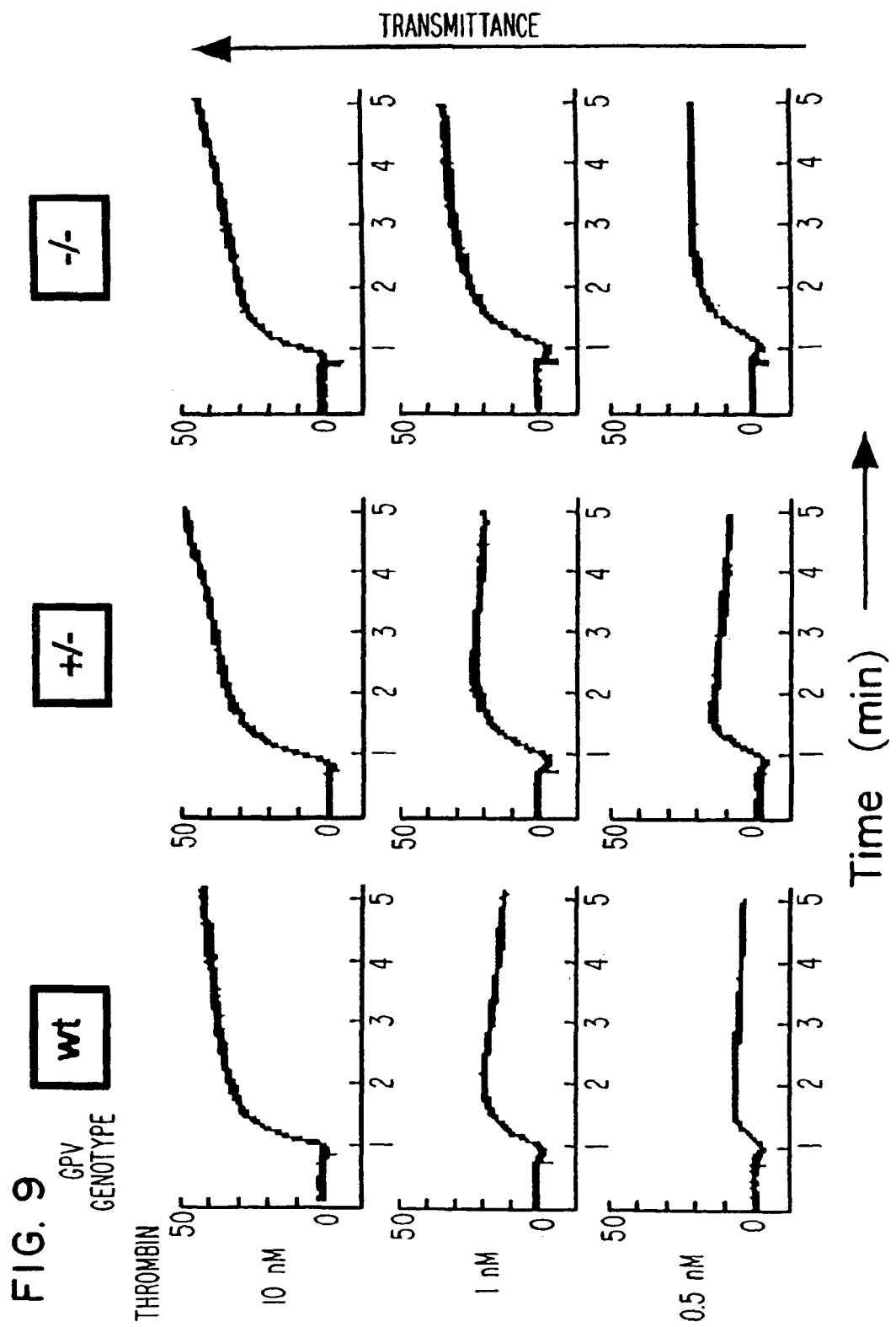

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: PCR primer
<221> NAME/KEY: variation
<222> LOCATION: (13)..(18)
<223> OTHER INFORMATION: y at position 13 = c or t; r at position
      18 = a or g.

<400> SEQUENCE: 1
ggcatgaccg tcytgcarcg                                                    20

<210> SEQ ID NO 2
<211> LENGTH: 7
<212> TYPE: PRT
<213> ORGANISM: Homo sapiens
<220> FEATURE:
<223> OTHER INFORMATION: Amino acid sequence corresponding to primer of
      seq. id no. 5.

<400> SEQUENCE: 2

Gly Met Thr Val Leu Gln Arg
 1               5

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: PCR primer
<221> NAME/KEY: variation
<222> LOCATION: (3)..(21)
<223> OTHER INFORMATION: y at position 3 = c or t; r at positions
      6 and 21 = a or g.

<400> SEQUENCE: 3
gayaaratgg tgytcytgga rca                                                23

<210> SEQ ID NO 4
<211> LENGTH: 8
<212> TYPE: PRT
<213> ORGANISM: Homo sapiens
<220> FEATURE:
<223> OTHER INFORMATION: Amino acid sequence corresponding to primer of
      seq. id no. 7.

<400> SEQUENCE: 4

Asp Lys Met Val Leu Leu Glu Gln
 1               5

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: PCR primer
<221> NAME/KEY: variation
<222> LOCATION: (3)..(24)
<223> OTHER INFORMATION: y at positions 3, 12, 15, 18 and 19 = c or t;
      v at position 6 = a or c or g; m at position 9 = a or
      c; s at position 24 = c or g.

<400> SEQUENCE: 5

-continued

```
ccyggvacmt tyagygayyt gatsaa                                              26
```

<210> SEQ ID NO 6
<211> LENGTH: 9
<212> TYPE: PRT
<213> ORGANISM: Homo sapiens

<400> SEQUENCE: 6

Pro Gly Thr Phe Ser Asp Leu Ile Lys
  1               5

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR primer
<221> NAME/KEY: variation
<222> LOCATION: (1)..(19)
<223> OTHER INFORMATION: r at positions 1, 7, 10, 13, 16 and
      19 = a or g; b at position 4 = c or g or t; k at position 6 =
      g or t.

<400> SEQUENCE: 7

```
rttbckraar gcrgcrgcrg g                                                   21
```

<210> SEQ ID NO 8
<211> LENGTH: 7
<212> TYPE: PRT
<213> ORGANISM: Homo sapiens
<220> FEATURE:
<223> OTHER INFORMATION: Amino acid sequence corresponding to the
      complementary strand of the primer in seq. id no.
      11.

<400> SEQUENCE: 8

Pro Ala Ala Ala Phe Arg Asn
  1               5

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: PCR primer
<221> NAME/KEY: variation
<222> LOCATION: (8)..(27)
<223> OTHER INFORMATION: r at positions 8, 12, 15, 18, 23 and 27
      = a or g; k at position 9 = g or t.

<400> SEQUENCE: 9

```
ggccccarkc crcartcrca garccarga                                           29
```

<210> SEQ ID NO 10
<211> LENGTH: 9
<212> TYPE: PRT
<213> ORGANISM: Homo sapiens

<400> SEQUENCE: 10

Ser Trp Arg Cys Asp Cys Gly Leu Gly
  1               5

<210> SEQ ID NO 11
<211> LENGTH: 3586
<212> TYPE: DNA
<213> ORGANISM: Mus musculus
<220> FEATURE:
<221> NAME/KEY: CDS
<222> LOCATION: (1411)..(3108)
<223> OTHER INFORMATION: Platelet glycoprotein V gene

<400> SEQUENCE: 11

```
gaattcattg gccttattta agaaataaaa tgttgagcaa agagatggc tcatcaggta      60
aagataccctc ccaagacatg gtgtgagtcc ttgggaacct acgtggagga aggtgagaac    120
caattgccta aagttttctg cacccacaa gtgaggcact gccacatgca cccacatact     180
cctgcacagg aatgagttag tgcaatgtag catggaaaaa aaccaaaagt gtggcccatg     240
taatgacagc ctgctatttc tgggaaaact taggccctct actctctagc ttttacaaaa    300
ggacttttaa ctatggactc tgaaagtttg aaagctcttg tcattaaaac ctagaatatg    360
ccctatggag atagtctttt tcttgacttt ttatctggta aggtctttat cttgaggatg    420
caagaatact tccctcttcc tctctgaagt gccaagtcac aagcagagct gcaagccttt    480
cagtcagtcc agggtgcaga actgcttcag gtaaggccaa atattcttaa attagtgtat    540
gcagttagag gctcagtctg tataggggca gaaggagacc tggtacaaga aacagtacaa    600
atttttactt gggaaacaga gtaaactagt attactgtgt gcttcctggg taactcaatg    660
cccagagtag ttttattaag cagcttggtg tataagcaaa cagtagctca ttatttaaat    720
gtgtgagtca gaaaaacatc ttcaaatgct acttatgtga cacttaaatt aacctcatgt    780
acactggagc gaccagccta ctgcactcgt gttactgtaa cagtgcaaag ttcagaaaag    840
catggcataa agcaatgggc attatcacct gcaccactgg gctccgggcc gggagttaca    900
aaacggtgta atgagttgtg gggtgttggt actttgaaaa tatgtaagaa attgaatcta    960
gtggaagtgg gccttgctgc ggttctcttg ctgactgttg gggataaagc tccctgctta   1020
acttgttaaa gtcagtgaca cagccagtcc caggaggcgt tgctttctat tctctgaaaa   1080
agaccgtagc aattttaatt cgttctgtaa cgattttaag gtattctgta gcttgaaaat   1140
gcccaaatgt caatgctcta aacagaaccg gggagatggc tgactggata aaaatgggaa   1200
cctgtaagac tgatctactc tccaataccc acatatgctg aatagaaaag taatttttt   1260
ttaatcagcc tttgtaagat agaggaagac ttggttgtat ctgagcgttc caaggccgtg   1320
agagtgctgg cccaaaaact gtgcttgcag cagtgcgtgc agggctccag gatatgctct   1380
gagccttgtt tttgctcttg catttcagac atg cta aga agc gcc ctg ctg tcc   1434
                                  Met Leu Arg Ser Ala Leu Leu Ser
                                    1               5
gcg gtg ctc gca ctc ttg cgt gcc caa cct ttt ccc tgc ccc aaa acc    1482
Ala Val Leu Ala Leu Leu Arg Ala Gln Pro Phe Pro Cys Pro Lys Thr
         10                  15                  20
tgc aag tgt gtg gtc cgc gat gcc gcg cag tgc tcg ggc ggc agc gtg    1530
Cys Lys Cys Val Val Arg Asp Ala Ala Gln Cys Ser Gly Gly Ser Val
 25                  30                  35                  40
gct cac atc gct gag cta ggt ctg cct acg aac ctc aca cac atc ctg    1578
Ala His Ile Ala Glu Leu Gly Leu Pro Thr Asn Leu Thr His Ile Leu
                 45                  50                  55
ctc ttc cga atg gac cag ggc ata ttg cgg aac cac agc ttc agc ggc    1626
Leu Phe Arg Met Asp Gln Gly Ile Leu Arg Asn His Ser Phe Ser Gly
             60                  65                  70
atg aca gtc ctt cag cgc ctg atg ctc tca gat agc cac att tcc gcc    1674
Met Thr Val Leu Gln Arg Leu Met Leu Ser Asp Ser His Ile Ser Ala
         75                  80                  85
atc gac ccc ggc acc ttc aat gac ctg gta aaa ctg aaa acc ctc agg    1722
Ile Asp Pro Gly Thr Phe Asn Asp Leu Val Lys Leu Lys Thr Leu Arg
     90                  95                 100
```

| | |
|---|---|
| ttg acg cgc aac aaa atc tct cgt ctt cca cgt gcg atc ctg gat aag<br>Leu Thr Arg Asn Lys Ile Ser Arg Leu Pro Arg Ala Ile Leu Asp Lys<br>105                    110                115                  120 | 1770 |
| atg gta ctc ttg gaa cag ctg ttc ttg gac cac aat gca cta agg gac<br>Met Val Leu Leu Glu Gln Leu Phe Leu Asp His Asn Ala Leu Arg Asp<br>                  125                  130                135 | 1818 |
| ctt gat caa aac ctg ttt cag caa ctg cgt aac ctt cag gag ctc ggt<br>Leu Asp Gln Asn Leu Phe Gln Gln Leu Arg Asn Leu Gln Glu Leu Gly<br>            140                145                150 | 1866 |
| ttg aac cag aat cag ctc tct ttt ctt cct gct aac ctt ttc tcg agc<br>Leu Asn Gln Asn Gln Leu Ser Phe Leu Pro Ala Asn Leu Phe Ser Ser<br>                155                160              165 | 1914 |
| ctg aga gaa ctg aag ttg ttg gat tta tcg cga aac aac ctg acc cac<br>Leu Arg Glu Leu Lys Leu Leu Asp Leu Ser Arg Asn Asn Leu Thr His<br>170                    175                180 | 1962 |
| ctg ccc aag gga ctg ctt ggg gct caa gtt aag ctt gag aaa ctg ctg<br>Leu Pro Lys Gly Leu Leu Gly Ala Gln Val Lys Leu Glu Lys Leu Leu<br>185                    190                195                200 | 2010 |
| ctc tat tca aac cag ctc acg tct gtg gat tcg ggg ctg ctg agc aac<br>Leu Tyr Ser Asn Gln Leu Thr Ser Val Asp Ser Gly Leu Leu Ser Asn<br>                205                210              215 | 2058 |
| ctg ggc gcc ctg act gag ctg cgg ctg gag cgg aat cac ctc cgc tcc<br>Leu Gly Ala Leu Thr Glu Leu Arg Leu Glu Arg Asn His Leu Arg Ser<br>            220                225                230 | 2106 |
| gta gcc ccg ggt gcc ttc gac cgc ctc gga aac ctg agc tcc ttg act<br>Val Ala Pro Gly Ala Phe Asp Arg Leu Gly Asn Leu Ser Ser Leu Thr<br>                235                240              245 | 2154 |
| cta tcc gga aac ctc ctg gag tct ctg ccg ccc gcg ctc ttc ctt cac<br>Leu Ser Gly Asn Leu Leu Glu Ser Leu Pro Pro Ala Leu Phe Leu His<br>250                    255                260 | 2202 |
| gtg agc agc gtg tct cgg ctg act ctg ttc gag aac ccc ctg gag gag<br>Val Ser Ser Val Ser Arg Leu Thr Leu Phe Glu Asn Pro Leu Glu Glu<br>265                    270                275                280 | 2250 |
| ctc ccg gac gtg ttg ttc ggg gag atg gcc ggc ctg cgg gag ctg tgg<br>Leu Pro Asp Val Leu Phe Gly Glu Met Ala Gly Leu Arg Glu Leu Trp<br>                285                290              295 | 2298 |
| ctg aac ggc acc cac ctg agc acg ctg ccc gcc gct gcc ttc cgc aac<br>Leu Asn Gly Thr His Leu Ser Thr Leu Pro Ala Ala Ala Phe Arg Asn<br>            300                305                310 | 2346 |
| ctg agc ggc ttg cag acg ctg ggg ctg acg cgg aac ccg cgc ctg agc<br>Leu Ser Gly Leu Gln Thr Leu Gly Leu Thr Arg Asn Pro Arg Leu Ser<br>                315                320              325 | 2394 |
| gcg ctc ccg cgc ggc gtg ttc cag ggc cta cgg gag ctg cgc gtg ctc<br>Ala Leu Pro Arg Gly Val Phe Gln Gly Leu Arg Glu Leu Arg Val Leu<br>330                    335                340 | 2442 |
| gcg ctg cac acc aac gcc ctg gcg gag ctg cgg gac gac gcg ctg cgc<br>Ala Leu His Thr Asn Ala Leu Ala Glu Leu Arg Asp Asp Ala Leu Arg<br>345                    350                355                360 | 2490 |
| ggc ctc ggg cac ctg cgc cag gtg tcg ctg cgc cac aac cgg ctg cgg<br>Gly Leu Gly His Leu Arg Gln Val Ser Leu Arg His Asn Arg Leu Arg<br>                365                370              375 | 2538 |
| gcc ctg ccc cgc acg ctc ttc cgc aac ctc agc agc ctc gag agc gtg<br>Ala Leu Pro Arg Thr Leu Phe Arg Asn Leu Ser Ser Leu Glu Ser Val<br>            380                385                390 | 2586 |
| cag cta gag cac aac cag ctg gag acg ctg cca gga gac gtg ttc gcg<br>Gln Leu Glu His Asn Gln Leu Glu Thr Leu Pro Gly Asp Val Phe Ala<br>                395                400              405 | 2634 |
| gct ctg ccc cag ctg acc cag gtc ctg ctg ggt cac aac ccc tgg ctc<br>Ala Leu Pro Gln Leu Thr Gln Val Leu Leu Gly His Asn Pro Trp Leu | 2682 |

-continued

```
            410                 415                 420
tgc gac tgt ggc ctg tgg ccc ttc ctc cag tgg ctg cgg cat cac ccg      2730
Cys Asp Cys Gly Leu Trp Pro Phe Leu Gln Trp Leu Arg His His Pro
425                 430                 435                 440 gac atc ctg ggc cga gac gag ccc ccg cag tgc cgt ggc ccg gag cca      2778
Asp Ile Leu Gly Arg Asp Glu Pro Pro Gln Cys Arg Gly Pro Glu Pro
                445                 450                 455 cgc gcc agc ctg tcg ttc tgg gag ctg ctg cag ggt gac ccg tgg tgc      2826
Arg Ala Ser Leu Ser Phe Trp Glu Leu Leu Gln Gly Asp Pro Trp Cys
            460                 465                 470 ccg gat cct cgc agc ctg cct ctc gac cct cca acc gaa aat gct ctg      2874
Pro Asp Pro Arg Ser Leu Pro Leu Asp Pro Pro Thr Glu Asn Ala Leu
        475                 480                 485 gaa gcc ccg gtt ccg tcc tgg ctg cct aac agc tgg cag tcc cag acg      2922
Glu Ala Pro Val Pro Ser Trp Leu Pro Asn Ser Trp Gln Ser Gln Thr
        490                 495                 500 tgg gcc cag ctg gtg gcc agg ggt gaa agt ccc aat aac agg ctc tac      2970
Trp Ala Gln Leu Val Ala Arg Gly Glu Ser Pro Asn Asn Arg Leu Tyr
505                 510                 515                 520 tgg ggt ctt tat att ctg ctt cta gta gcc cag gcc atc ata gcc gcg      3018
Trp Gly Leu Tyr Ile Leu Leu Leu Val Ala Gln Ala Ile Ile Ala Ala
                525                 530                 535 ttc atc gtg ttt gcc atg att aaa atc ggc cag ctg ttt cga aca tta      3066
Phe Ile Val Phe Ala Met Ile Lys Ile Gly Gln Leu Phe Arg Thr Leu
            540                 545                 550 ata aga gag aag ctc ttg tta gag gca atg gga aaa tcg tgt              3108
Ile Arg Glu Lys Leu Leu Leu Glu Ala Met Gly Lys Ser Cys
        555                 560                 565 aactaatgaa actgaccaga gcattgtgga cggggcccca aggagaatgc agtcaggatg    3168
ctggcgtgcc attacactat ttcccaggcc ttttctcctc tcccgtgctc ttagtgtctc    3228
ttcttctccc ctctcttcag aagtagcttt tgtaaatcgc tactgctttc tagcctggcc    3288
tgggttacct cctctgctgt tagtttcaag ggggctgagg gtgggggttc gacgggactt    3348
ggctcatcag gtccaactgt gcagcgctgg gtgcctagtg gagagaggag cccttttcttg   3408 gtttctgaat ttgaggacac atcctgccag tgggcaagac ctctccggga cccagcaagg    3468
gttgagtaac atttgctgaa ggaacaccgg cttaaaacga accctaggtc caagagatga    3528
aggctcttcc caaaataaag gtggagtgtt cttgtccctt tacctgaaag gagaattc      3586
```

<210> SEQ ID NO 12
<211> LENGTH: 566
<212> TYPE: PRT
<213> ORGANISM: Mus musculus

<400> SEQUENCE: 12

```
Met Leu Arg Ser Ala Leu Leu Ser Ala Val Leu Ala Leu Leu Arg Ala
1               5                   10                  15

Gln Pro Phe Pro Cys Pro Lys Thr Cys Lys Cys Val Val Arg Asp Ala
                20                  25                  30

Ala Gln Cys Ser Gly Gly Ser Val Ala His Ile Ala Glu Leu Gly Leu
            35                  40                  45

Pro Thr Asn Leu Thr His Ile Leu Leu Phe Arg Met Asp Gln Gly Ile
        50                  55                  60

Leu Arg Asn His Ser Phe Ser Gly Met Thr Val Leu Gln Arg Leu Met
65                  70                  75                  80

Leu Ser Asp Ser His Ile Ser Ala Ile Asp Pro Gly Thr Phe Asn Asp
                85                  90                  95
```

-continued

```
Leu Val Lys Leu Lys Thr Leu Arg Leu Thr Arg Asn Lys Ile Ser Arg
            100                 105                 110
Leu Pro Arg Ala Ile Leu Asp Lys Met Val Leu Glu Gln Leu Phe
        115                 120                 125
Leu Asp His Asn Ala Leu Arg Asp Leu Asp Gln Asn Leu Phe Gln Gln
        130                 135                 140
Leu Arg Asn Leu Gln Glu Leu Gly Leu Asn Gln Asn Gln Leu Ser Phe
145                 150                 155                 160
Leu Pro Ala Asn Leu Phe Ser Ser Leu Arg Glu Leu Lys Leu Leu Asp
                165                 170                 175
Leu Ser Arg Asn Asn Leu Thr His Leu Pro Lys Gly Leu Leu Gly Ala
            180                 185                 190
Gln Val Lys Leu Glu Lys Leu Leu Leu Tyr Ser Asn Gln Leu Thr Ser
        195                 200                 205
Val Asp Ser Gly Leu Leu Ser Asn Leu Gly Ala Leu Thr Glu Leu Arg
    210                 215                 220
Leu Glu Arg Asn His Leu Arg Ser Val Ala Pro Gly Ala Phe Asp Arg
225                 230                 235                 240
Leu Gly Asn Leu Ser Ser Leu Thr Leu Ser Gly Asn Leu Leu Glu Ser
                245                 250                 255
Leu Pro Pro Ala Leu Phe Leu His Val Ser Ser Val Ser Arg Leu Thr
            260                 265                 270
Leu Phe Glu Asn Pro Leu Glu Glu Leu Pro Asp Val Leu Phe Gly Glu
        275                 280                 285
Met Ala Gly Leu Arg Glu Leu Trp Leu Asn Gly Thr His Leu Ser Thr
    290                 295                 300
Leu Pro Ala Ala Ala Phe Arg Asn Leu Ser Gly Leu Gln Thr Leu Gly
305                 310                 315                 320
Leu Thr Arg Asn Pro Arg Leu Ser Ala Leu Pro Arg Gly Val Phe Gln
                325                 330                 335
Gly Leu Arg Glu Leu Arg Val Leu Ala Leu His Thr Asn Ala Leu Ala
            340                 345                 350
Glu Leu Arg Asp Asp Ala Leu Arg Gly Leu Gly His Leu Arg Gln Val
        355                 360                 365
Ser Leu Arg His Asn Arg Leu Arg Ala Leu Pro Arg Thr Leu Phe Arg
    370                 375                 380
Asn Leu Ser Ser Leu Glu Ser Val Gln Leu Glu His Asn Gln Leu Glu
385                 390                 395                 400
Thr Leu Pro Gly Asp Val Phe Ala Ala Leu Pro Gln Leu Thr Gln Val
                405                 410                 415
Leu Leu Gly His Asn Pro Trp Leu Cys Asp Cys Gly Leu Trp Pro Phe
            420                 425                 430
Leu Gln Trp Leu Arg His His Pro Asp Ile Leu Gly Arg Asp Glu Pro
        435                 440                 445
Pro Gln Cys Arg Gly Pro Glu Pro Arg Ala Ser Leu Ser Phe Trp Glu
    450                 455                 460
Leu Leu Gln Gly Asp Pro Trp Cys Pro Asp Pro Arg Ser Leu Pro Leu
465                 470                 475                 480
Asp Pro Pro Thr Glu Asn Ala Leu Glu Ala Pro Val Pro Ser Trp Leu
                485                 490                 495
Pro Asn Ser Trp Gln Ser Gln Thr Trp Ala Gln Leu Val Ala Arg Gly
            500                 505                 510
```

```
Glu Ser Pro Asn Asn Arg Leu Tyr Trp Gly Leu Tyr Ile Leu Leu Leu
        515                 520                 525

Val Ala Gln Ala Ile Ile Ala Ala Phe Ile Val Phe Ala Met Ile Lys
        530                 535                 540

Ile Gly Gln Leu Phe Arg Thr Leu Ile Arg Glu Lys Leu Leu Leu Glu
545                 550                 555                 560

Ala Met Gly Lys Ser Cys
                565

<210> SEQ ID NO 13
<211> LENGTH: 7452
<212> TYPE: DNA
<213> ORGANISM: Homo sapiens
<220> FEATURE:
<221> NAME/KEY: CDS
<222> LOCATION: (2422)..(4101)
<223> OTHER INFORMATION: Platelet glycoprotein V gene

<400> SEQUENCE: 13
```

| | | | | | |
|---|---|---|---|---|---|
| tgatcggaac | tgaaagacct | cccgcgatac | ctggcagagg | cagtggctct | tccctgtggt | 60 |
| ccagggctga | ctgactttga | aggtaatttc | agtcaaccca | gcctttactg | ggctctgact | 120 |
| gcattaggct | gcatcaaagg | ggattggatc | ccatgattct | ttatatcttc | tgacattaag | 180 |
| cctttgtcag | ctataggtgt | tacaaatatc | tttagtttgt | ggtttatctt | ttccccttt | 240 |
| ttatggtgtc | ttgaaggata | gaagtcttaa | tgcagacagc | attatcagtg | tgttcaaaag | 300 |
| acagctagac | acgttttgcc | tatagacaaa | tgggcaaaag | gaaacccagc | tttctcaaat | 360 |
| gaagcacaag | tgggccttaa | ttatgtgaaa | aggtgttcaa | gttcatcatt | aaacagggaa | 420 |
| aggaaaagtt | aaaaccatgc | tgagatatct | tcatagaaaa | tggcaaaaag | caggaagtgc | 480 |
| cacgtgtggg | cagagaggaa | gcacaggaac | tctcacaaat | ggcaggtgtc | atcgtagacc | 540 |
| aacacaacca | cttggagag | cagtttgact | ttccccagtt | aaactgaaca | tgtgagcggc | 600 |
| cgggcgtggt | ggctcatgcc | tgtaatccca | gcagtttggg | aggccgaggc | gggcggattg | 660 |
| cctgagctca | ggagttcaag | accagccagg | gcaacacggt | aaaacccgt | ctctactaaa | 720 |
| atacaaaaaa | ttagctgggc | gtgatggtgt | gtgcctgtaa | tcccagctac | ttgtgaggcc | 780 |
| gaggcaggag | aattgcttga | accagggagc | aggaggttgc | agtgagccga | gatcgcacca | 840 |
| ctgcacccca | gcctggcgac | agagtccccc | tcccccacca | aaaaacaac | aagtgagcat | 900 |
| cctgcaacct | agcaatgcca | ttgttgaaca | agttcaaaga | tgttcttagc | cttattagtc | 960 |
| ccaaaaggaa | gaaaaaaatg | gaggatttga | gaatgttctt | agctttattg | ctaagcggag | 1020 |
| aaagaaaaac | aacacatacc | aaaaaaaaaa | aaaaaaaaa | aaaaaaacaa | aaaacctggg | 1080 |
| tgggaaatta | gggccatgtg | gcatgaaaag | gaagacccag | gggaagtgtg | gcccatctag | 1140 |
| gggtgtggct | actgcagtga | tccagctgta | tcactgaact | tccctggcat | catagagtta | 1200 |
| tattgtgcca | tttatggaaa | aactctcccc | actgctcttg | gctttgacag | taggaatcag | 1260 |
| gttatatatg | gtctctcggt | ttgaagatat | ttgtcattaa | aaaccagaac | aagggctctg | 1320 |
| agatagggtc | ctttcctgac | ctactctggt | aaagtcttta | tcctcaggat | gcaaggatac | 1380 |
| caccctcttc | ctgtggaaag | tgtcgaatca | catgcagagc | tctaagtctt | tcagttactt | 1440 |
| tggagtgcag | aaccatttca | ggtaaggcca | aatattttaa | acattagtat | aggaaattag | 1500 |
| agggctcttt | agtctgtgtg | tgcatgagaa | gtaaaattgc | acgagaagca | atttatgtaa | 1560 |
| aatttcgctt | aggaaacatt | gttttggcag | gttagtagta | tggtgtgcat | ttcccagaaa | 1620 |
| attcagtgcc | gtgagtatta | cctttagtta | agcatcttag | aaatagtagc | tctttatgtt | 1680 |

```
tatggctaag tcagaaatac taccctcaaa ttctatgtga ccctagttat actgttgagc    1740
ctttctgtgc ctctgtgcct tcatccttga atcggggata atatacttac ctcctaaggt    1800
tattgtaagg attaaatgca tgtagtataa ataaagagct gagaacaatg catggcgtaa    1860
agtgataggt attattatat gcttttgttg gctgttgatt gaaggtgttc gctgttttgg    1920
gggtgtcctt taatagagta acttggtact gtggaaatag catgattgtg agcaaaagaa    1980
tcagatggtg gtggctgcag actttgctgt tcccttcttg actgttggtt atagccaatg    2040
cagggtaagt tataaagtca agagcagagc cgttttcaca atggacattg ctttgtgatg    2100
tctgtgagct tgaatgtgag aatgattatt ttaattctct atgtaaagac tttaaagtat    2160
tggctattcg gtagcttgaa aactctgtaa tctcatgctt taaactgaga gtggaaaatc    2220
aataaagcaa aagcatgagg ccacgcagtg tagaatgagt gtcttttcac cacgtaggga    2280
aatctgtagt cctaagaaaa gagggagtga gaattctggc gaaaagattg tgcctctgca    2340
caaagtgcag gatcccaggg ttcagtacag gcgcgaacgc tcctgtgtgt tgaccacact    2400
cccacggttg cttttcaga c atg ctg agg ggg act cta ctg tgc gcg gtg       2451
                       Met Leu Arg Gly Thr Leu Leu Cys Ala Val
                         1               5                  10 ctc ggg ctt ctg cgc gcc cag ccc ttc ccc tgt ccg cca gct tgc aag      2499
Leu Gly Leu Leu Arg Ala Gln Pro Phe Pro Cys Pro Pro Ala Cys Lys
                15                  20                  25 tgt gtc ttc cgg gac gcc gcg cag tgc tcg ggg ggc gac gtg gcg cgc      2547
Cys Val Phe Arg Asp Ala Ala Gln Cys Ser Gly Gly Asp Val Ala Arg
             30                  35                  40 atc tcc gcg ctg ggc ctg ccc acc aac ctc acg cac atc ctg ctc ttc      2595
Ile Ser Ala Leu Gly Leu Pro Thr Asn Leu Thr His Ile Leu Leu Phe
         45                  50                  55 gga atg ggc cgc ggc gtc ctg cag agc cag agc ttc agc ggc atg acc      2643
Gly Met Gly Arg Gly Val Leu Gln Ser Gln Ser Phe Ser Gly Met Thr
     60                  65                  70 gtc ctg cag cgc ctc atg atc tcc gac agc cac att tcc gcc gtt gcc      2691
Val Leu Gln Arg Leu Met Ile Ser Asp Ser His Ile Ser Ala Val Ala
 75                  80                  85                  90 ccc ggc acc ttc agt gac ctg ata aaa ctg aaa acc ctg agg ctg tcg      2739
Pro Gly Thr Phe Ser Asp Leu Ile Lys Leu Lys Thr Leu Arg Leu Ser
                 95                 100                 105 cgc aac aaa atc acg cat ctt cca ggt gcg ctg ctg gat aag atg gtg      2787
Arg Asn Lys Ile Thr His Leu Pro Gly Ala Leu Leu Asp Lys Met Val
             110                 115                 120 ctc ctg gag cag ttg ttt ttg gac cac aat gcg cta agg ggc att gac      2835
Leu Leu Glu Gln Leu Phe Leu Asp His Asn Ala Leu Arg Gly Ile Asp
         125                 130                 135 caa aac atg ttt cag aaa ctg gtt aac ctg cag gag ctc gct ctg aac      2883
Gln Asn Met Phe Gln Lys Leu Val Asn Leu Gln Glu Leu Ala Leu Asn
     140                 145                 150 cag aat cag ctc gat ttc ctt cct gcc agt ctc ttc acg aat ctg gag      2931
Gln Asn Gln Leu Asp Phe Leu Pro Ala Ser Leu Phe Thr Asn Leu Glu
155                 160                 165                 170 aac ctg aag ttg ttg gat tta tcg gga aac aac ctg acc cac ctg ccc      2979
Asn Leu Lys Leu Leu Asp Leu Ser Gly Asn Asn Leu Thr His Leu Pro
                 175                 180                 185 aag ggg ttg ctt gga gca cag gct aag ctc gag aga ctt ctg ctc cac      3027
Lys Gly Leu Leu Gly Ala Gln Ala Lys Leu Glu Arg Leu Leu Leu His
             190                 195                 200 tcg aac cgc ctt gtg tct ctg gat tcg ggg ctg ttg aac agc ctg ggc      3075
```

```
                                    -continued

Ser Asn Arg Leu Val Ser Leu Asp Ser Gly Leu Leu Asn Ser Leu Gly
    205                 210                 215 gcc ctg acg gag ctg cag ttc cac cga aat cac atc cgt tcc atc gca      3123
Ala Leu Thr Glu Leu Gln Phe His Arg Asn His Ile Arg Ser Ile Ala
    220                 225                 230 ccc ggg gcc ttc gac cgg ctc cca aac ctc agt tct ttg acg ctt tcg      3171
Pro Gly Ala Phe Asp Arg Leu Pro Asn Leu Ser Ser Leu Thr Leu Ser
235                 240                 245                 250 aga aac cac ctt gcg ttt ctc ccc tct gcg ctc ttt ctt cat tcg cac      3219
Arg Asn His Leu Ala Phe Leu Pro Ser Ala Leu Phe Leu His Ser His
                255                 260                 265 aat ctg act ctg ttg act ctg ttc gag aac ccg ctg gca gag ctc ccg      3267
Asn Leu Thr Leu Leu Thr Leu Phe Glu Asn Pro Leu Ala Glu Leu Pro
            270                 275                 280 ggg gtg ctc ttc ggg gag atg ggg ggc ctg cag gag ctg tgg ctg aac      3315
Gly Val Leu Phe Gly Glu Met Gly Gly Leu Gln Glu Leu Trp Leu Asn
        285                 290                 295 cgc acc cag ctg cgc acc ctg ccc gcc gcc gcc ttc cgc aac ctg agc      3363
Arg Thr Gln Leu Arg Thr Leu Pro Ala Ala Ala Phe Arg Asn Leu Ser
    300                 305                 310 cgc ctg cgg tac tta ggg gtg act ctg agc ccg cgg ctg agc gcg ctt      3411
Arg Leu Arg Tyr Leu Gly Val Thr Leu Ser Pro Arg Leu Ser Ala Leu
315                 320                 325                 330 ccg cag ggc gcc ttc cag ggc ctt ggc gag ctc cag gtg ctc gcc ctg      3459
Pro Gln Gly Ala Phe Gln Gly Leu Gly Glu Leu Gln Val Leu Ala Leu
                335                 340                 345 cac tcc aac ggc ctg acc gcc ctc ccc gac ggc ttg ctg cgc ggc ctc      3507
His Ser Asn Gly Leu Thr Ala Leu Pro Asp Gly Leu Leu Arg Gly Leu
            350                 355                 360 ggc aag ctg cgc cag gtg tcc ctg cgc cgc aac agg ctg cgc gcc ctg      3555
Gly Lys Leu Arg Gln Val Ser Leu Arg Arg Asn Arg Leu Arg Ala Leu
        365                 370                 375 ccc cgt gcc ctc ttc cgc aat ctc agc agc ctg gag agc gtc cag ctc      3603
Pro Arg Ala Leu Phe Arg Asn Leu Ser Ser Leu Glu Ser Val Gln Leu
    380                 385                 390 gac cac aac cag ctg gag acc ctg cct ggc gac gtg ttt ggg gct ctg      3651
Asp His Asn Gln Leu Glu Thr Leu Pro Gly Asp Val Phe Gly Ala Leu
395                 400                 405                 410 ccc cgg ctg acg gag gtc ctg ttg ggg cac aac tcc tgg cgc tgc gac      3699
Pro Arg Leu Thr Glu Val Leu Leu Gly His Asn Ser Trp Arg Cys Asp
                415                 420                 425 tgt ggc ctg ggg ccc ttc ctg ggg tgg ctg cgg cag cac cta ggc ctc      3747
Cys Gly Leu Gly Pro Phe Leu Gly Trp Leu Arg Gln His Leu Gly Leu
            430                 435                 440 gtg ggc ggg gaa gag ccc cca cgg tgc gca ggc cct ggg gcg cac gcc      3795
Val Gly Gly Glu Glu Pro Pro Arg Cys Ala Gly Pro Gly Ala His Ala
        445                 450                 455 ggc ctg ccg ctc tgg gcc ctg ccg ggg ggt gac gcg gag tgc cgg ggc      3843
Gly Leu Pro Leu Trp Ala Leu Pro Gly Gly Asp Ala Glu Cys Pro Gly
    460                 465                 470 ccc cgg ggc ccg cct ccc cgc ccc gct gcg gac agc tcc tcg gaa gcc      3891
Pro Arg Gly Pro Pro Pro Arg Pro Ala Ala Asp Ser Ser Ser Glu Ala
475                 480                 485                 490 cct gtc cac cca gcc ttg gct ccc aac agc tca gaa ccc tgg gtg tgg      3939
Pro Val His Pro Ala Leu Ala Pro Asn Ser Ser Glu Pro Trp Val Trp
                495                 500                 505 gcc cag ccg gtg acc acg ggc aaa ggt caa gat cat agt ccg ttc tgg      3987
Ala Gln Pro Val Thr Thr Gly Lys Gly Gln Asp His Ser Pro Phe Trp
            510                 515                 520
```

-continued

| | |
|---|---|
| ggg ttt tat ttt ctg ctt tta gct gtt cag gcc atg atc acc gtg atc<br>Gly Phe Tyr Phe Leu Leu Leu Ala Val Gln Ala Met Ile Thr Val Ile<br>    525                        530                      535 | 4035 |
| atc gtg ttt gct atg att aaa att ggc caa ctc ttt cga aaa tta atc<br>Ile Val Phe Ala Met Ile Lys Ile Gly Gln Leu Phe Arg Lys Leu Ile<br>    540                        545                      550 | 4083 |
| aga gag aga gcc ctt ggg taaaccaatg gaaaatctt ctaattactt<br>Arg Glu Arg Ala Leu Gly<br>555                560 | 4131 |
| agaacctgac cagatgtggc tcggagggga atccagaccc gctgctgtct tgctctccct | 4191 |
| cccctcccca ctcctcctct cttcttcctc ttctctctca ctgccacgcc ttcctttccc | 4251 |
| tcctcctccc cctctccgct ctgtgctctt cattctcacg ggcccgcaac ccctcctctc | 4311 |
| tctgtccccg cccgtctctg gaaactgagc ttgacgtttg taaactgtgg ttgcctgcct | 4371 |
| tcccagctcc acgcggtgtg cgctgacact gccgggggc tggactgtgt tggacccatc | 4431 |
| cttgccccgt gtgcctggc ttggcctctg gtggagagag ggacctcttc agtgtctact | 4491 |
| gagtaagggg acagctccag gccggggctg tctcctgcac agagtaagcc ggtaaatgtt | 4551 |
| tgtgaaatca atgcgtggat aaaggaacac atgccatcca agtgatgatg cttttcctg | 4611 |
| gagggaaagg ataggctgtt gctctatcta atttttttgtt tttgttttg gacagtctag | 4671 |
| ctctgtggcc caggctggcg tgcagtgggc cgtctcagtt cactgcagcc tccgccctcc | 4731 |
| aggttcaagt gattctcatg cctcagcgtt ctgagtagct gggattagag gcgtgtgcca | 4791 |
| ctacacccgg ctaattttg tacttttaa agtagagacg ggctttgcca tattggcctg | 4851 |
| gctgatctca aactcctggt cttgaactcc tggccacaag tgatctgccc gccttagcct | 4911 |
| cccaaagtgc tgggattaca ggcgcaagcc actacacctg ccctcttcat cgaatttat | 4971 |
| ttgagaagta gagctcttgc catttttcc cttgctccat tttctcact ttatgtctct | 5031 |
| ctgacctatg ggctacttgg gagagcactg gactccattc atgcatgagc attttcagga | 5091 |
| taagcgactt ctgtgaggct gagagaggaa gaaaacacgg agccttccct ccaggtgccc | 5151 |
| agtgtaggtc cagcgtgttt cctgagcctc ctgtgagttt ccacttgctt tacatccatg | 5211 |
| caacatgtca ttttgaaact ggattgattt gcatttcctg gaactctgcc acctcatttc | 5271 |
| acaagcattt atggagcagt taacatgtga ctggtattca tgaatataat gataagcttg | 5331 |
| attctagttc agctgctgtc acagtctcat ttgttcttcc aactgaaagc cgtaaaacct | 5391 |
| ttgttgcttt aattgaatgt ctgtgcttat gagaggcagt ggttaaaaca ttttctggcg | 5451 |
| agttgacaac tgtgggttca atcccagct ctaccactta ctaactgcat gggactttgg | 5511 |
| gtaagacacc tgcttacatt ctctaagcct tggtttcctg aaccttaaaa caggataaca | 5571 |
| tagtacctgc ttcatagagt tttgtgagaa ttaaaggcaa taaagcatat aatgacttag | 5631 |
| cccagcggcc tgcagacaat acatgttaat gaatgttagc tattattact aaagatgagc | 5691 |
| aattattatt ggcatcatga tttctaaaga agagctttga gttggtattt ttctctgtgt | 5751 |
| ataagggtaa gtccgaactt tctcatactg gaggttacat tcacatcagt ctgtcttccc | 5811 |
| ctgcggatgg cctcagccct gggtggccag gctctgtgct cacagtccag agcaatggat | 5871 |
| cctccaacac caccaggtgg atgtggagca ggagagctgg atcgtggcat tgtttctgg | 5931 |
| gttctgcagt tgggagttgg tttctgggtt ctccattggt ctacttgtct agtcccatac | 5991 |
| cagactcacg gtctccatta ttggagcttt aataatttt ggtatagggt catctctcca | 6051 |
| ccttgttttt cttctattct tggttctttg caattctatg aatatttcag ggtcagcatg | 6111 |
| tcaactccat tgaaaaaccc tgctgggatt ttaatagaac ttacagctca cgcctgtaat | 6171 |

-continued

```
cccagcactt tgggaggctg aggtgggtgg atcacaggtc aggagtttga gaacagctgg    6231
ccaagatggt gaaaccccgt ctctactaaa aatacaaaaa ttagctgggt gcggtggcag    6291
gtgcctgtag tcccagctac ttgggacacc gaggcaggag aatcacttga acccgggagg    6351
cggaggttgc agtgagccga gatcgtgcca ctgcactcta gcctgggcga cagagcgaga    6411
ctccatctca aaaaaaaaga aaagaaaat  tgcagtaaat ttaaaactaa tttggggaag    6471
aatctgtatt tttacaatac ctagtgttct tgccagtaag catggttcat cttcccattt    6531
atttacgtca ttttaaatct ttcagtgatg ttttagaatt ttttttataa aaaccttcac    6591
tataagaaca gaaaaccaaa caccgcatgt tctcactcat aggtgggaat tgaacaatga    6651
gaacacttgg acacagggcg gggaacgtca cacgcctgga ctgttggggg ggtggctggg    6711
agagggatag tgttaggaga aatacctaat gtaaatgacg agttaatggt gcagccaacc    6771
aacctggcac atgtattcat atgtaacaaa cctgcacgtt gtgcacatgt accctagaac    6831
ttaaagtata ttaaaaaaag aaaccttggc actgattttg ttagatttat tcctaggtat    6891
ccttcctctt ttttgatttg tcattgctat tgtagatggc atcttttaa  aaagttatat    6951 tttctaaagc aaaaaataaa aaagttgta  tttctaattt ttattaccaa tatataagaa    7011
tgtaatttat ttttacataa ttatcttatg tctagtaata attctgataa tttgcttctt    7071
cctattaaaa ccttacaccc attattgatt tattttctg  ttttaaaata tcttcctgca    7131
ctggctaaaa cctccactat aatgttgagc agaacagtga ggcatcctta gaactatctt    7191
ggttgcaaag ggtaggtctc taatgttttca tcaataaatg tgatgtttct agtctgagtt    7251
tgctaagtat attttaaaat aatcagtaaa gttagatttt atccattttt atcttaacta    7311
ttgagatgct catatcattt ttcttcttca atgtgttaaa atggtgaata aatttataga    7371
ttttggaaaa gtaaattcat tcttgcattc ccgaagtaaa ccaagccatg ctatgtgtat    7431
ttaaaatata ttgctgaatt c                                              7452
```

<210> SEQ ID NO 14
<211> LENGTH: 560
<212> TYPE: PRT
<213> ORGANISM: Homo sapiens

<400> SEQUENCE: 14

```
Met Leu Arg Gly Thr Leu Leu Cys Ala Val Leu Gly Leu Leu Arg Ala
  1               5                  10                  15

Gln Pro Phe Pro Cys Pro Pro Ala Cys Lys Cys Val Phe Arg Asp Ala
                 20                  25                  30

Ala Gln Cys Ser Gly Gly Asp Val Ala Arg Ile Ser Ala Leu Gly Leu
             35                  40                  45

Pro Thr Asn Leu Thr His Ile Leu Leu Phe Gly Met Gly Arg Gly Val
         50                  55                  60

Leu Gln Ser Gln Ser Phe Ser Gly Met Thr Val Leu Gln Arg Leu Met
 65                  70                  75                  80

Ile Ser Asp Ser His Ile Ser Ala Val Ala Pro Gly Thr Phe Ser Asp
                 85                  90                  95

Leu Ile Lys Leu Lys Thr Leu Arg Leu Ser Arg Asn Lys Ile Thr His
            100                 105                 110

Leu Pro Gly Ala Leu Leu Asp Lys Met Val Leu Leu Glu Gln Leu Phe
        115                 120                 125

Leu Asp His Asn Ala Leu Arg Gly Ile Asp Gln Asn Met Phe Gln Lys
    130                 135                 140
```

-continued

```
Leu Val Asn Leu Gln Glu Leu Ala Leu Asn Gln Asn Gln Leu Asp Phe
145                 150                 155                 160

Leu Pro Ala Ser Leu Phe Thr Asn Leu Glu Asn Leu Lys Leu Leu Asp
                165                 170                 175

Leu Ser Gly Asn Asn Leu Thr His Leu Pro Lys Gly Leu Leu Gly Ala
            180                 185                 190

Gln Ala Lys Leu Glu Arg Leu Leu Leu His Ser Asn Arg Leu Val Ser
        195                 200                 205

Leu Asp Ser Gly Leu Leu Asn Ser Leu Gly Ala Leu Thr Glu Leu Gln
210                 215                 220

Phe His Arg Asn His Ile Arg Ser Ile Ala Pro Gly Ala Phe Asp Arg
225                 230                 235                 240

Leu Pro Asn Leu Ser Ser Leu Thr Leu Ser Arg Asn His Leu Ala Phe
                245                 250                 255

Leu Pro Ser Ala Leu Phe Leu His Ser His Asn Leu Thr Leu Leu Thr
            260                 265                 270

Leu Phe Glu Asn Pro Leu Ala Glu Leu Pro Gly Val Leu Phe Gly Glu
        275                 280                 285

Met Gly Gly Leu Gln Glu Leu Trp Leu Asn Arg Thr Gln Leu Arg Thr
290                 295                 300

Leu Pro Ala Ala Ala Phe Arg Asn Leu Ser Arg Leu Arg Tyr Leu Gly
305                 310                 315                 320

Val Thr Leu Ser Pro Arg Leu Ser Ala Leu Pro Gln Gly Ala Phe Gln
                325                 330                 335

Gly Leu Gly Glu Leu Gln Val Leu Ala Leu His Ser Asn Gly Leu Thr
            340                 345                 350

Ala Leu Pro Asp Gly Leu Leu Arg Gly Leu Gly Lys Leu Arg Gln Val
        355                 360                 365

Ser Leu Arg Arg Asn Arg Leu Arg Ala Leu Pro Arg Ala Leu Phe Arg
370                 375                 380

Asn Leu Ser Ser Leu Glu Ser Val Gln Leu Asp His Asn Gln Leu Glu
385                 390                 395                 400

Thr Leu Pro Gly Asp Val Phe Gly Ala Leu Pro Arg Leu Thr Glu Val
                405                 410                 415

Leu Leu Gly His Asn Ser Trp Arg Cys Asp Cys Gly Leu Gly Pro Phe
            420                 425                 430

Leu Gly Trp Leu Arg Gln His Leu Gly Leu Val Gly Gly Glu Glu Pro
        435                 440                 445

Pro Arg Cys Ala Gly Pro Gly Ala His Ala Gly Leu Pro Leu Trp Ala
450                 455                 460

Leu Pro Gly Gly Asp Ala Glu Cys Pro Gly Pro Arg Gly Pro Pro Pro
465                 470                 475                 480

Arg Pro Ala Ala Asp Ser Ser Glu Ala Pro Val His Pro Ala Leu
                485                 490                 495

Ala Pro Asn Ser Ser Glu Pro Trp Val Trp Ala Gln Pro Val Thr Thr
            500                 505                 510

Gly Lys Gly Gln Asp His Ser Pro Phe Trp Gly Phe Tyr Phe Leu Leu
        515                 520                 525

Leu Ala Val Gln Ala Met Ile Thr Val Ile Val Phe Ala Met Ile
530                 535                 540

Lys Ile Gly Gln Leu Phe Arg Lys Leu Ile Arg Glu Arg Ala Leu Gly
545                 550                 555                 560
```

TRANSGENIC ANIMALS HAVING A MODIFIED GLYCOPROTEIN V GENE

CROSS REFERENCES TO RELATED APPLICATIONS

This application is a continuation of international application PCT/US99/17594 filed Aug. 4, 1999 which claims priority to U.S. provisional patent application 60/109,797 filed Aug. 4, 1998 the disclosures of which are herein incorporated by reference in their entirety.

FIELD OF THE INVENTION

The present invention relates to nonhuman, transgenic animals in which the Glycoprotein V (GP V) gene has been modified so that the animals do not express a functional GP V protein or express a GP V protein that demonstrates a reduced functionality as compared with the native or wild-type GP V protein. Such modifications may be accomplished, for example, through inactivation of the GP V gene by deletion or through targeted disruption of its genomic coding region. In particular, the present invention relates to a nonhuman, transgenic mammal, such as a mouse or rat, that does not express a GP V protein or that expresses a modified GP V protein. The present intention also relates to transgenic animal model systems and to transgenic, isolated cell model systems usefull to identify agents that modulate the effects of such a GP V modification. In particular, the isolated cell model system relates to platelets isolated from such transgenic animals.

BACKGROUND OF THE INVENTION

The GPIb-IX-V complex is a large multimeric protein complex on the platelet surface which consists of 4 different subunits GPIbα, GPIbβ, GPIX and GP V in the ratio of 2:2:2:1. Absence of some or all of the subunits of this complex results in a severe recessive bleeding disorder known as Bernard-Soulier syndrome (Blood (1998) 91(12): 4397–4418). The GPIbα subunit contains the high affinity binding site for thrombin and the binding site for vWf. This complex has been implicated in the initial events associated with arterial thrombosis (Savage et al. (1996) Cell 84:289–297 and Weiss (1995) Thrombosis and Haemostasis 74(1):117–122).

It is known that GP V is a platelet and endothelial cell specific glycoprotein, and that it is a substrate for thrombin. It also is known that the activation of platelets by thrombin results in the loss of surface GP V. However, the precise role that GP V plays in the function of the GPIb-IX-V complex has not been described.

SUMMARY OF THE INVENTION

The present invention provides nonhuman transgenic animals, preferably mammals, that contain or comprise a modified GP V gene. The genomic GP V gene of such transgenic animals has been modified in the sense that it has been deleted, in whole or in part, or that it has been altered, substituted or mutated in some way. The particular modification is not critical so long as the cells of the transgenic animal do not express a GP V protein, do not express a functional GP V protein or express a GP V protein that demonstrates a modified (i.e., reduced) functionality as compared with the same type of cell that expresses the native or wild-type GP V protein. Examples of mammals contemplated by the present invention include sheep, goats, mice, pigs, dogs, cats, monkeys, chimpanzees, hamsters, rats, rabbits, cows and guinea pigs.

The present invention also provides cells isolated from such animals, including platelets and other blood cells isolated from the blood of the transgenic non-human animals according to the present invention.

The present invention also provides methods of preparing a nonhuman transgenic animal, preferably a mammal, with a modified GP V gene. Such modification may be accomplished by techniques that are known in the art and that are discussed below.

The present invention also provides methods of comparing a characteristic between two mammals of the same species, or strain, wherein one mammal has, for example, a wild-type GP V gene and the other mammal has an modified GP V gene. The present invention similarly provides methods for comparing cells isolated from such mammals.

The present invention also provides methods of determining the effect of various agents on selected biological characteristics of a genetically engineered animal expressing a modified GP V gene, wherein the methods comprise: a) administering the agent to the genetically engineered animal; b) maintaining the animal for a desired period of time after administration of the agent; and c) determining whether a characteristic of the animal that is attributable to the expression of the modified GP V gene has been affected by the administration of said agent. The present invention similarly provides methods for determining the effects of various agents on the phenotypical, physiological, or biological characteristics of cells isolated from such genetically engineered animals.

BRIEF DESCRIPTION OF THE DRAWINGS

FIGS. 1A–1C show the murine DNA sequence of GP V (SEQ ID NO: 11).

FIG. 2 shows the murine GP V amino acid sequence (SEC ID NO: 12).

FIGS. 3A–3C show the human DNA sequence of GP V (SEQ ID NO: 13).

Figure 4:
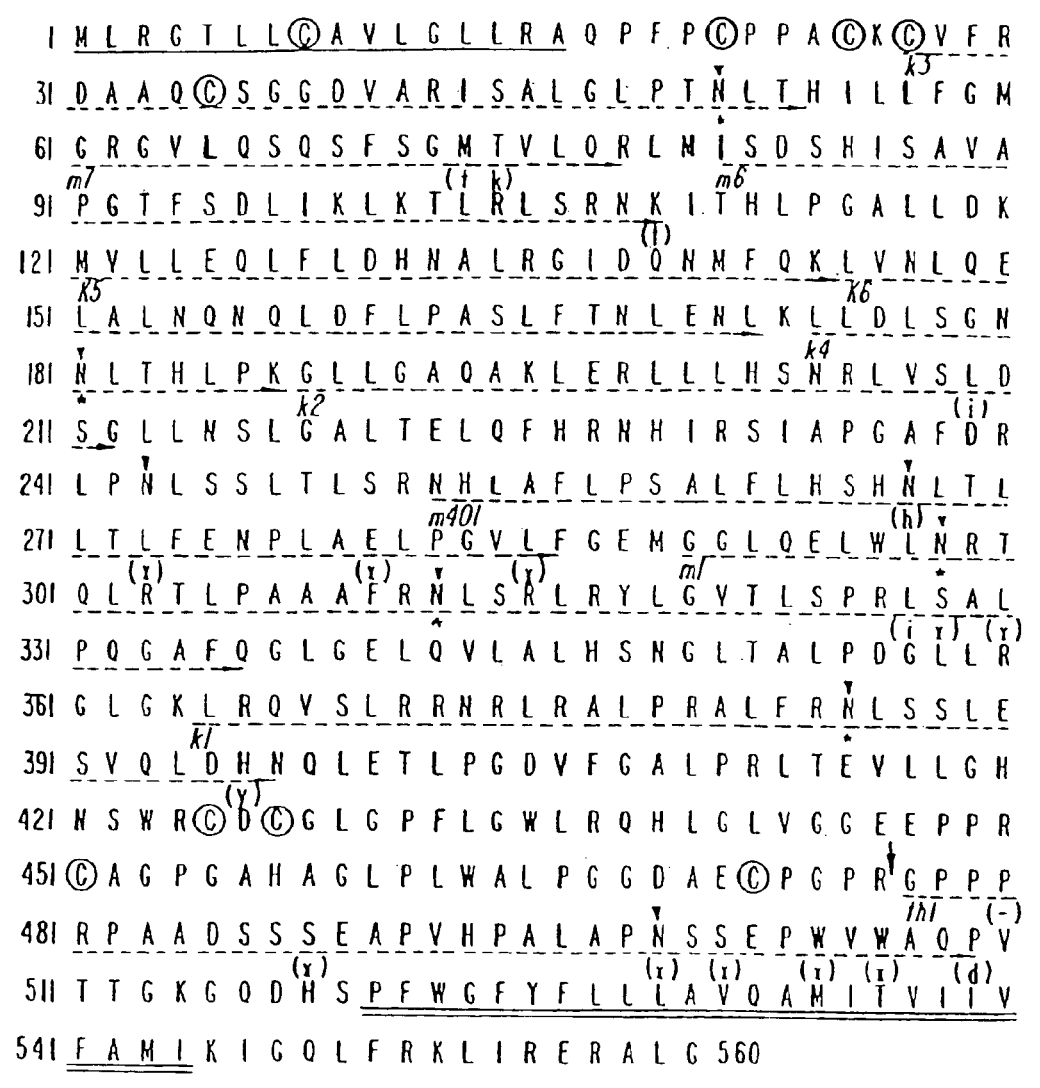

FIG. 4 shows the human GP V amino acid wequence (SEQ ID NO:14).

FIG. 9 shows thrombin-induced aggregation in washed platelets from GP V wt, +/- and -/- mice. WP were prepared from 6-10 mice of each genotype, which were littermate controls. Platelet aggregation was determined in an aggregometer (Chrono-Log Corp). Five such experiments were carried out, and 4 out of five worked in the manner shown.

DETAILED DESCRIPTION

Figure 5:
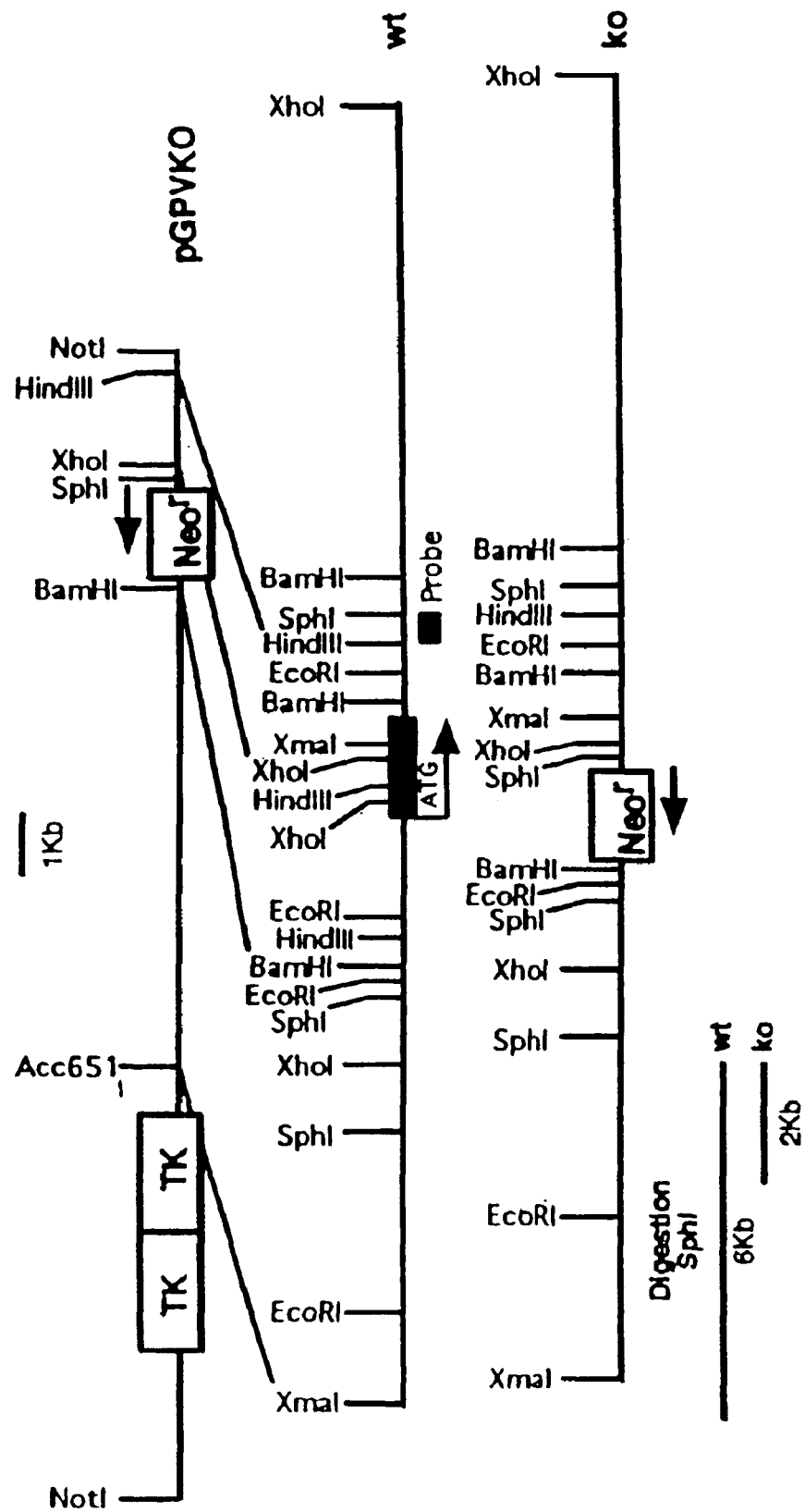
FIG. 5 shows the genomic organization of the mouse GP V gene and structure of the targeting vector pGP VKO. Mouse GP V was mapped from a BAC ES129 library and a 5' homology region (8 Kb) consisting of the Xma1 (blunt)-Bam H1 fragment was cloned into the Acc 651(blunt)-BamHI sites on the vector pPN2T, and the 3' homology region (1.4 Kb) consisting of the XhoI-HindIII was cloned into the corresponding sites around the Neo$^r$ cassette, as shown.

The present invention relates to the production and use of nonhuman transgenic animals, preferably mammals, that contain or comprise a modified GP V gene. Specifically, the genomic GP V gene of such transgenic animals has been modified in the sense that it has been deleted, in whole or in part, or that it has been altered, substituted or mutated in some way. Particularly contemplated are those modifications in which the cells of the transgenic animal do not express a functional GP V protein or express a GP V protein that demonstrates a reduced functionality as compared with the same type of cell that expresses the native or wild-type GP V protein. Thus, the nature of a particular modification is not critical so long as transgenic animal or transgenic cells contain or express such a modified GP V gene. The present invention also relates to cells isolated from such transgenic animals. Particularly contemplated are platelets and other blood cells isolated from the blood of the transgenic nonhuman animals according to the present invention.

FIGS. 1A-1C provide the DNA sequence of the mouse GP V gene. In one aspect of the present invention, transgenic animals containing or expressing modified sequences of this GP V-encoding DNA sequence can be generated using knock-out procedures that are known in the art to disrupt the genomic gene. A variety of known procedures are contemplated, such as targeted recombination. Once generated, such a transgenic or genetically-engineered animal, for example, a "knock-out mouse", can be used to 1) identify biological and pathological processes mediated by GP V; 2) identify proteins and other genes that interact with the GP V protein; 3) identify agents that can be exogenously supplied to overcome the absence or reduction in GP V protein function; and 4) serve as an appropriate screen for identifying agents that modulate (i.e., increase or decrease) the activity of the transgenic cells of knock-out mice or other animals so modified.

In general, a transgenic nonhuman animal according to the present invention may be prepared by producing a vector containing an appropriately modified GP V genomic sequence and then transfecting such a vector into embryonic stem cells (ES Cells) of that animal species. For example, in the production of a transgenic mouse according to the present invention, transfected mouse ES Cells that had undergone a homologous recombination event at the GP V locus were then identified by restriction analysis Southern blotting. The desired modified ES cells were then injected into blastocysts in order to generate chimeric mice which were bred to wild-type mice to produce heterozygote animals expressing one normal and one modified GP V allele (as assessed by Southern blotting of tail genomic DNA). Through conventional breeding techniques thereafter, heterozygotic (or chimeric) females may then be crossed with chimeric males to generate homozygotes.

Platelets from such transgenic mice can be used in a number of assays to identify agents that modulate GP V function or to assess the role of GP V in platelet function. For example, the bleeding time of modified or transgenic mice can be monitored in a screening assay to identify agents that improve or restore the wild-type clotting phenotype. Such assays also may help to elucidate the extent to which GP V is critical for normal hemostasis.

In a preferred embodiment of the present invention, a mouse was generated in which the GP V gene was modified by targeted disruption of the GP V coding region to inactivate the GP V gene. The platelets from these animals may be expected to show certain phenotypic effects resulting from the loss of a fully-functional GP V gene (and expression product) on both the expression and function of the GPIb-IX-V complex. Specifically, the intact transgenic animals and cells derived from such animals may be used to evaluate the activity of various agents that modulate GP V function. Such animals and cells also provide a model system useful in evaluating the consequences of GP V cleavage on the function of the GPIb-IX-V complex and in identifying agents useful in modulating these consequences.

Unless defined otherwise, all technical and scientific terms used in this application have the same meaning as would commonly be understood by a person having an ordinary level of skill in the field to which this invention belongs. Although any methods and materials similar or equivalent to those described herein can be used in the practice or testing of the present invention, the preferred methods and materials are described.

For example, the term "animal" is used herein to include all vertebrate animals including mammals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass an animal produced by classical cross-breeding alone or by in vitro fertilization alone, but rather is meant to encompass animals in which one or more cells are altered by or receive a recombinant, exogenous or cloned DNA molecule. This molecule may be specifically targeted to a defined genetic locus, be randomly integrated within a chromosome, or it may be extrachromosomally replicating DNA.

The term "knock-out" generally refers to mutant organisms, usually mice, which contain a null or non-functional allele of a specific gene. The term "knock-in" generally refers to mutant organisms, also usually mice, into which a gene has been inserted through homologous recombination. The knock-in gene may be a mutant form of a gene which replaces the endogenous, wild-type gene. Non-functional GP V genes include GP V genes which have been modified or inactivated, in whole or in part, by mutation or via any available method so that GP V expression is prevented, disrupted or altered so as to disrupt the wild type GP V phenotype. Such mutations include insertions of heterologous sequences, deletions, frame shift mutations and any other mutations that prevent, disrupt or alter GP V expression.

The transgenic mammals of the present invention therefore may display non-normal platelet aggregation and/or other effects. By comparing the physiological and morphological characteristics between the transformed and non-transformed animals, one skilled in the art can thereby determine the effect of the presence or absence of the GP V gene and its expression product on the corresponding animal.

The transgenic animals of the present invention can also be used to identify agents that modulate (i.e., either promote or further inhibit) platelet aggregation or other effects that are mediated by the GPIb-IX-V complex. The evaluation of such agents can be conducted either in vitro, in situ, or in vivo by techniques known to those skilled in the art.

The cells, platelets, tissues and whole organisms of the disclosed transgenic animals specifically have utility in testing the effect of various agents for their ability to reduce or increase GPIb-IX-V complex mediated processes. Agents that can be tested include various anticoagulant, thrombolytic and antiplatelet therapeutics and drugs. Examples of such agents include glycosaminoglycans such as heparin; oral anticoagulants such as dicumarol, anisindione, and bromadkiolone; tissue plasminogen activator (t-PA); urokinase; aspirin; dipyridamole; and ticlopidine. See, Majerus, et al., *Anticoagulant, Thrombolytic, and Antiplatelet Drugs*, in Goodman & Gilman's The Pharmacological Basis of Therapeutics, Ninth Edition, Chapter 54 (1996) for a more complete list of such agents and their pharmacology.

The cells and whole organisms of the transgenic animals of the present invention, quite apart from their uses in veterinary and human medicine, may also be used to investigate gene regulation, expression and organization in animals. In general, for further examples of diagnostic and research uses of transgenic mammals, especially transgenic mice, see U.S. Pat. No. 5,569,824.

Homologous Recombination Techniques

Genes that are modified, truncated or replaced in whole or in part can be introduced into a target cell in a site directed fashion using homologous recombination. Similarly, homologous recombination techniques may be used to introduce a DNA sequence into the cells of an organism where a particular gene has been deleted from its native position in that sequence. Papers discussing homologous recombination are discussed in R. Kucherlapati et al., (1995) U.S. Pat. No. 5,413,923. Through these technique, for example, a DNA sequence in which the GP V gene has been modified or deleted can be introduced. Such methods result in the creation of a transgenic animal, wherein the animal's genome has been modified, and the phenotype of the modified animal or cells from the modified animal can be studied for purposes of drug screening, investigating physiologic processes, developing new products and the like.

Homologous recombination permits site-specific modifications in endogenous genes and thus inherited or acquired mutations may be corrected, and/or novel alterations may be engineered into the target animal's genome. To prepare cells for homologous recombination in the generation of transgenic animals, embryonic stem cells or a stem cell line may be obtained. Cells other than embryonic stem cells can be utilized (e.g., hematopoietic stem cells, etc.) See, for more examples, J. G. Seidman et al., (1994) U.S. Pat. No. 5,589,369. The cells may be grown on an appropriate fibroblast fetal layer or grown in the presence of leukemia inhibiting factor (LIF) and then used. Once transformed, the embryonic stem cells may be injected into a blastocyst that has been previously obtained, to provide a chimeric animal.

The main advantage of the embryonic stem cell technique is that the cells transfected with the "transgene" can be tested, prior to reimplantation into a female animal for gestation, to assess integration of the transgene and the effect of the transgene. In contrast to the conventional microinjection technique, the homologous respective endogenous gene can be removed from a chromosome by homologous recombination with the transgene. By subsequent cross-breeding experiments, animals can be bred which carry the transgene on both chromosomes. If mutations are incorporated into the transgenes which block expression of the normal gene, the endogenous genes can be eliminated by this technique and functional studies can thus be performed for purposes described above.

Homologous recombination can also proceed extrachromasomally, which may be of benefit when handling large gene sequences (e.g., larger than 50 kb). Methods of performing extrachromosomal homologous recombination are described in R. M. Kay et al., (1998) U.S. Pat. No. 5,721,367.

Production of Transgenic Animals

Transgenic animals are genetically modified animals into which recombinant, exogenous or cloned genetic material has been experimentally transferred. Such genetic material is often referred to as a "transgene". The nucleic acid sequence of the transgene may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The development of transgenic technology allows investigators to create animals of virtually any genotype and to assess the consequences of introducing specific foreign nucleic acid sequences on the physiological and morphological characteristics of the transformed animals. In general, the availability of transgenic animals permits cellular processes to be influenced and examined in a systematic and specific manner not achievable with most other test systems. For example, the development of transgenic animals provides biological and medical scientists with models that are useful in the study of disease. Such animals are also useful for the testing and development of new pharmaceutically active substances.

Transgenic animals can be produced by a variety of different methods including transfection, electroporation, microinjection, gene targeting in embryonic stem cells and recombinant viral and retroviral infection (see, e.g., U.S. Pat. Nos. 4,736,866; 5,602,307; Mullins et al. (1993) Hypertension 22(4):630633; Brenin et al. (1997) Surg. Oncol. 6(2)99–110; Tuan (ed.), *Recombinant Gene Expression Protocols*, Methods in Molecular Biology No. 62, Humana Press (1997)).

A number of recombinant or transgenic mice have been produced, including those which express an activated oncogene sequence (U.S. Pat. No. 4,736,866); express simian SV 40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al. (1996) Genetics 143(4):1753–1760); and, are capable of generating a fully human antibody response (McCarthy (1997) The Lancet 349(9049):405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. (1997) Mol. Reprod. Dev. 46(4):515–526; Houdebine (1995) Reprod. Nutr. Dev. 35(6):609–617; Petters (1994) Reprod. Fertil. Dev. 6(5): 643–645; Schnieke et al. (1997) Science 278(5346): 2130–2133; and Amoah (1997) J. Animal Science 75(2): 578–585).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. Nos. 5,489,743 and 5,602,307.

Without further description, it is believed that one of ordinary skill in the art can, using the preceding description and the following illustrative examples, make and utilize the compositions of the present invention and practice the claimed methods. The following working examples therefore, specifically point out preferred embodiments of the present invention, and are not to be construed as limiting in any way the remainder of the disclosure.
Other generic configurations will be apparent to one skilled in the art Methods Proteins and Antibodies.

Rabbit antibodies against peptides based on mouse GP V generated by standard methods (Harlow, E. & Lane, D. (1988) *Antibodies: A Laboratory Manual* (Cold Spring Harbor Laboratory, Cold Spring Harbor)) include Ab #810 (against mouse GP V residues $C^{472}$-$A^{490}$) and Ab#808 (against mouse GP V residues $L^{432}$-$R^{450}$). Anti-GP Ib-IX (rabbit polyclonal Ab #3584) was kindly provided by Dr. Beat Steiner, Hoffman-LaRoche (22). Anti-αIIbβ3 (Ab #41) was described previously (Law, D. A, Nannizzi-Alaimo, L., Ministri, K, Hughes, P. E., Forsyth, J., Turner, M., Shattil, S. J., Ginsberg, M. H., Tybulewicz, V. L. & Phillips, D. R. (1999) *Blood* 93, 2645–52).

Human fibrinogen (Enzyme Research Labs) or human vWf (Haematologic technologies) were FITC-labeled in 0.1M NaHCO₃ (1 mg/mL) using FITC~celite (Molecular Probes). Labeling conditions were designed to obtain F/P ratios between 1 and 4.

Snake venom peptide botrocetin was purified as described from the venom of Bothrops jaracaca (Andrews, R. K., Booth, W. J., Gorman, J. J., Castaldi, P. A. & Berndt, M. C. (1989) *Biochemistry* 28, 8317–26) and kindly provided by J. Rose. Human glycocalicin was purified from outdated platelets as described (Vicente, V., Kostel, P. J. & Ruggeri, Z. M. (1988) *J Biol Chem* 263, 18473–9) by affinity chromatography using mouse anti-human glycocalicin (MAb 5A12; kindly provided by Dr. Burt Adelman).

Generation of the GP V –/– Mouse.

Rat platelet RNA was isolated using RNAzol from fresh rat platelets and the GP V coding region (700 bp) obtained by RT-PCR using degenerate primers based on the human GP V sequence (Lanza, F., Morales, M., de La Salle, C., Cazenave, J. P., Clemetson, K. J., Shimomura, T. & Phillips, D. R. (1993) *J Biol Chem* 268,20801–7), was cloned into pCR2.1 (Invitrogen) and sequenced. The rat GP V insert was used to screen a mouse 129 BAC library (Genome Systems) and 2 positive clones (11487 and 11488) were identified.

Genomic DNA was isolated and a detailed map of ~22 Kb of the mouse GP V generated (FIG. 5). The 5' XmaI fragment (11 Kb) and the EcoR1 fragment (4 Kb, containing the mouse GP V gene) were isolated from BAC plasmid DNA, subcloned into BlueScript (Statagene), and sequenced. The mouse 129 GP V coding sequence showed 91% homology to the rat coding sequence, compared to 71% to human GP V.

The ~8 Kb XmaI(blunt)-BamHI fragment from the XmaI plasmid was first subcloned into the vector pPN2T (Tybulewicz, V. L., Crawford, C. E., Jackson, P. K., Bronson, R. T. & Mulligan, R. C. (1991) *Cell* 65, 1153–63; Morrison, J. R., Paszty, C., Stevens, M. E., Hughes, S. D., Forte, T., Scott, J. & Rubin, E. M. (1996) *Proc Natl Acad Sci USA* 93, 7154–9) at the Acc651(blunt)-BamHI sites to generate the 5' homology region (HR) downstream of the Neo$^r$ cassette, followed by the 1.4 Kb XhoI-HindIII fragment from the EcoRI plasmid generating the 3' HR upstream of the Neo$^r$ cassette. Thus in the recombinant, the coding region of mouse GP V (including the putative initiator Met) to Leu$^{389}$ was replaced by a Neo$^r$ cassette oriented transcriptionally in the opposite direction (FIG. 5). pGP VKO was electroporated into the ES cell line RW4 (Hug, B. A., Wesselschmidt, R. L., Fiering, S., Bender, M. A., Epner, E., Groudine, M. & Ley, T. J. (1996) *Mol Cell Biol* 16, 2906–12.).

Neo$^r$ clones were identified by positive selection in G418 media Recombinants were microinjected into embryos from C57BL/6J mice using standard techniques (Dr. R. Wesselschmidt, Genome Systems). One of several chimeric males generated was bred with C57BL/6J females. Confirmation of recombination and germline transmission were performed using a probe designed to show linkage following SphI digestion of genomic DNA (10 μg) isolated as described (Laird, P. W., Zijderveld, A., Linders, K., Rudnicki, M. A., Jaenisch, R. & Berns, A. (1991) *Nucleic Acids Res* 19,4293) and Southern analysis. Heterozygote (+/–) animals identified by Southern blotting were bred to homozygosity.

Mouse Platelet Preparation.

Blood from anaesthetized mice was obtained by cardiac puncture diluted into saline contain g 1/10 vol of either (a) TSC buffer (3.8% trisodium citrate, 0.111M glucose, pH 7, 0.4 μM prostaglandin E1 (PGE1)) for platelet-rich plasma (PRP) or (b) Acid-Citrate-Dextrose (ACD, 85 mM sodium citrate, 0.111M glucose, 714 mM citric acid, 0.4 μM PGE1), for washed platelets (WP). Diluted blood was centrifuged at 82×g for 10 min.

The supernatant from (a) normalized to 2×10⁸ platelets/mL and 1 mM Mg$^{2+}$ (final) was PRP. For WP, the supernatant from (b) was pooled with a second obtained by centrifugation after the repeat addition of 137 mM NaCl, and centrifuged at 325×g for 10 min.

Platelets were washed twice in CGS buffer (12.9 mM sodium citrate, 33.33 mM glucose, and 123.2 mM NaCl, pH7) and resuspended in calcium-free Tyrodes-Hepes buffer (CFTH; 10 mM Hepes, 5.56 mM glucose, 137 mM NaCl, 12 mM NaHCO₃, 2.7 mM KCl, 0.36 mM NaH₂PO₄, 1 mM MgCl₂, pH7.4). Platelets were normalized to 2×10⁸/ml. PRP or WP were incubated at room temp for 30 min prior to use.

Glycoprotein Expression.

Flow cytometry was carried out as follows: PRP (10 μl) was incubated with primary rabbit antibody in CFTH containing 0.1% BSA for 1 hour at 4° C., followed by phycoerythrin (PE)-conjugated donkey anti-rabbit IgG (H+L) F(ab')$_2$ (1:200, Jackson ImmunoResearch) for 30 min at 4° C. in the dark. Samples were diluted to 400 μL in PBS containing 0.1% BSA and analyzed on a FACSORT (Becton-Dickinson).

Western analysis was carried out as follows: WP (5×10$^7$) were solubilized in reducing sample buffer (Laemmli, U. K. (1970) *Nature* 227, 680–5), electrophoresed, transferred to membranes and probed with primary rabbit antibody overnight at 4° C. Blots were incubated with peroxidase conjugated mouse anti-rabbit secondary antibody (1:5000; Jackson ImmunoResearch) for 1 hour at 4° C. and developed by ECL (Amersham).

FITC~Ligand Binding Assay.

For the determination of solution-phase vWf binding, pooled PRP was incubated with FITC~vWf and botrocetin (4 μM–40 μM) for 10 min. Samples were diluted in CFTH buffer prior to analysis. For FITC~fibrinogen binding, WP were isolated from individual mice and incubated in duplicate (1×10$^6$) α-thrombin for 10 min. The reaction was terminated with PPACK (phenylalaninylprolylargininylchloromethylketone; 50 μM final). The platelets were incubated with FTIC~labeled fibrinogen (100 μgs/ml) for 30 min, fixed with p-formaldehyde (10%) for 20 min and diluted into 1% p-formaldehyde in CFTH and analyzed by flow cytometry.

Binding Assays.

96-well plates were coated with various concentrations (25–500 ng/well) of human vWf overnight at 4° C. Pooled WP from mice were resuspended in Mg$^{2+}$-free CFTH buffer (1.2×10$^8$/mL) containing botrocetin (4 μM), and incubated immobilized human vWf for 1 hour at room temp. Following two PBS washes, bound platelets were lysed and intracellular acid phosphatase activity was quantitated calorimetrically using the substrate pNPP (Sigma).

Platelet Aggregation.

Each experiment used pooled WP from 6–10 littermate mice of each genotype. Platelet aggregation initiated by thrombin was measured in a lumi-aggregometer (Chrono-Log) with stirring (100–1200 rpm) at 37° C.

Determination of Bleeding Time.

Bleeding time measurements were obtained using the tail cut model (Hodivala-Dilke, K. M., McHugh, K. P., Tsakiris, D. A., Rayburn, H., Crowley, D., Ullman-Cullere, M., Ross, F. P., Coller, B. S., Teitelbaum, S. & Hynes, R. O. (1999) *J Clin Invest* 103, 229–38) on littermate mice generated from heterozygous breeding. Since complete litters were not used the numbers of wt to +/– and –/– do not reflect Mendelian ratios. All experiments were blinded.

Briefly, anaesthetized mice were transected at the 5 mm mark from the tip of tail and incubated in warm (37° C.) saline. The time for cessation of bleeding was noted as the primary endpoint. If bleeding did not stop in 15 min, the tail was cauterized and 900 sec noted as the bleeding time. Data are presented as mean±sem, and statistical significance was assessed using both Student's t-test analysis and Mann-Whitney nonparametric analysis.

EXAMPLES

Example 1

Generation of the Targeting Vector

1. Obtaining the Murine GP V Genomic DNA

The sequence of murine GP V was unknown at the start of this project. We therefore generated degenerate primers based on the human GP V sequence which had been published (Lanza et al (1993), J. Biol. Chem., Vol 268 (28) pp20801–20807. U.S. patent application Ser. No. 08/089, 455, filed Jul. 9, 1993, abondoned, which is incorporated by reference herein and FIGS. 3A–3C). These primers had the following sequences:

Coding Sequences:

5' GGCATGACCGTC(CT)TGCA(GA)CG (SEQ ID NO: 1) which corresponds to human GP V residues GMTVLQR (SEQ ID NO: 2).

5' GA(CT)AA(AG)ATGGT(CT)TC(CT)TGGA(GACA (SEQ ID NO: 3) corresponds to human GP V residues DKMVLLEQ (SEQ ID NO: 4).

5' CC(CT)GG(CGA)AC(AC)TT(TC)AG(CT)GA(CT)(CT)TGA(GC)AA 3' (SEQ ID NO: 5) corresponds to human GP V residues PGTFSDLIK (SEQ ID NO: 6).

Complements of Portions of the Human GP V Coding Sequence

5' (AG)TT(TGC)C(TG)(AG)AA(AG)GC(AG)GC(AG)GC(AG)GG 3'(SEQ ID NO: 7) corresponds to the complement of the human GP V sequence encoding PAAAFRN (SEQ ID NO: 8)

5'GGCCCCA(AG)(TG)CC(AG)CA(AG)TC(AG)CAGA(AG)CCA(AG)GA 3'(SEQ ID NO: 9) corresponds to the complement of the human GP V sequence encoding SWRCDCGLG (SEQ ID NO: 10).

Fresh rat platelets were isolated by standard techniques and RNA was isolated using RNAzol. PolyA$^+$ RNA was generated using the Oligo-Tex system. cDNA was prepared from the polyA$^+$ RNA using the In-Vitrogen cDNA cycle lit. The cDNA was then used in PCR reactions with each combination of the primers listed above.

All PCR reaction products were then cloned into pCR2.1 cloning vectors from the In-Vitrogen TA cloning kit. GIBCO SURE competent cells were transformed using the manufacturer's protocol and white (transformant) colonies were selected. Miniprep DNA was generated by the rapid boiling method and restriction analysis was used to identify the clones containing inserts of the right size (~700 bp). Several clones were expanded for sequencing. Sequence analysis showed that clone B1–12 was homologous to the human GP V gene, and was the rat homologue of the GP V gene.

The insert from this clone was isolated and used to screen the mouse 129 BAC library (Genome Systems) by hybridization (see Shizuya et aL (1992) Proceed. Natl. Acad. Sci. USA 89:8794–8797). 2 clones 11487 and 11488 were positive. Genomic DNA was isolated from these clones. Approximately –22Kb of the insert was mapped using Southern blotting with the BI-12 insert. The mouse genomic DNA for GP V was identified by homology to the published human GP V DNA sequence (FIGS. 1A–1C and FIG. 2).

2. Construction of the Targeting Vector.

The vector pPN2T (10.15 Kb) is a modified version of the pPNT vector (Tybulewicz et al (1991) Cell 65:1153–1163, Morrison et al (1996) Proc. Natl. Acad Sci. USA 93: 7154–7159) which, in addition to the Neo resistance (Neo$^r$) cassette, has 2 contiguous herpes simplex virus thymidine kiase (TK) cassettes (instead of the single one in pPNT) and a pUC vector backbone. BAC plasmid DNA was isolated from clone 11488 using protocols supplied by Genome Systems. We isolated a 11–16 Kb Xma1 fragment and a ~4 Kb EcoR1 fragment which were subcloned into BlueScript. The Xma1 containing plasmid was used to generate a ~8 Kb Xma1-BamH1 fragment which was blunted using Klenow at the Xma1 site. This fragment was then subcloned into the targeting vector pPN2T at the Acc651(blunt)-BamH1 sites in the polylinker which was at the 3' end of the Neo$^r$ cassette between the Neo$^r$ and TK cassettes, such that its orientation was opposite to that of the Neo gene. The 1.4 Kb Xho1-

HindIII 3' homology region was isolated from the BAC plasmid DNA using the same methodology, and subcloned into BlueScript and the cut out using Xho1-Not1. This Xho1-Not1 fragment was then inserted into the targeting vector at the 5' end of the Neo$^r$ cassette. The final targeting vector pGP VKO had the mouse GP V homology regions in the opposite orientation from that of the Neo gene.

Example 2

Generation of ES Cells

The targeting vector was inserted into the ES cell line RW4 by electroporation by standard techniques (Genome Systems® and Hug et al. (1996) Mol. Cell. Biol. 16(6): 2906–2912). Neo$^r$ clones were identified by positive selection in G418 media Identification of the targeted ES cells which had undergone recombination was done using the restriction enzyme Sph 1 to digest the genomic DNA from the clones and Southern blotting with a probe designed to show linkage (outside probe).

Clone 367 was shown to be recombinant since Southern blot analysis showed the expected 2 bands, one at 6 Kb (wild type allele) and one at 2 Kb (recombinant) and was then micro-injected into embryos from C57B16 mice using standard techniques. Several chimeric males were generated which were then bred with C57B16 females to determine germline transmission.

Example 3

Generation of GP V Knock-Out Mice

To evaluate the specific role of GP V in both platelet function and the GP Ib-IX-V complex expression, we generated a mouse strain that lacked the GP V gene using homologous recombination techniques (Koller, B. H. & Smithies, O. (1992) Annu Rev Immunol 10, 705–30). Since rat GP V RNA would have greater homology to mouse GP V than the cloned human gene and was easier to isolate than mouse platelet RNA, rat platelet RNA for GP V was isolated and used as a probe for isolating genomic mouse GP V which was mapped and cloned from a BAC 129/Sv library.

Complete sequencing of 3 separate clones showed the mouse 129/Sv GP V gene to have 99.9% homology in the coding region to the published mouse C57BL/6J mouse sequence (Ravanat, C., Morales, M., Azorsa, D. O., Moog, S., Schuhler, S., Grunert, P., Loew, D., Van Dorsselaer, A., Cazenave, J. P. & Lanza, F. (1997) Blood 89, 3253–62) at both the DNA and protein levels (not shown). Sequencing also proved that the mouse and rat coding sequences were more homologous (DNA=92%, protein=87%), than human and mouse GP V (DNA=78%, protein=70%).

Recombinants were selected based on Southern analysis using the probe shown in FIG. 5 and two recombinants were used to generate the founder chimeras. One of these founder males (>85% chimeric) was successfully mated with C57BL/6J females to produce +/− offspring, which were bred to generate homozygotes. Deficiency in the GP V gene has not affected viability at birth as evidenced by findings that the litters have expected Mendelian ratios of −/− offspring (1:4) and that the GP V −/− animals are fertile with no gross observable defects.

Analysis of whole blood from GP V-deficient animals showed the platelets were normal in both number and size. Platelet counts in whole blood were within the normal range {wt males=$6.52 \times 10^8$/ml (n=17) and females=$5.6 \times 10^8$/ml (n=8); +/− males=$7.56 \times 10^8$/ml (n=15) and females =$5.12 \times 10^8$/ml (n=12); −/− males=$7.02 \times 10^8$/ml (n=21) and females=$5.36 \times 10^8$/ml (=9)}. There was a statistically significant difference in platelet recovery from whole blood from wt animals (males=74±22%; females=82.4±13%) and −/− animals (males=62±19.5%, p=0.05; females=67±14%, p=0.03). +/− animals showed intermediate recovery numbers, which were not statistically different {males= 71±19%, $p_{(wt\ to\ +/-)}$=0.55 and $p_{(+/-\ to\ -/-)}$=0.14; and females= 78±12%, $p_{(wt\ to\ +/-)}$32 0.46 and $p_{(+/-\ to\ -/+)}$ =0.065}.

Platelets were isolated from the −/− animals to conform that gene deletion resulted in absence of GP V protein expression and analyzed for GP V expression using GP V antibodies. No GP V protein was detectable either on the intact platelet surface using FACS analysis or in total platelet lysates as determined by Western blotting.

Example 4

Effect of GP V Gene Deletion on GP Ib-IX Expression and Function

GP V is usually expressed in platelets as a complex with GP Ib-IX (Meyer, S. C. & Fox, J. E. (1995) J Biol Chem 270, 14693–9; Modderman, P. W., Admiraal, L. G., Sonnenberg, A. & von dem Borne, A. E. (1992) J Biol Chem 267, 364–9).

We used two techniques to determine whether absence of GP V from the platelet surface affected the expression of the other subunits of the GP Ib-IX-V complex. FACS analysis using an antibody specific for GP Ib-IX showed similar levels of GP Ib-IX in all three genotypes (Mean relative fluorescence units (RFU)±sd for wt=547±106; +/−=391±65; −/−=483±56 with $p_{(wt\ to\ -/-)}$ =0.42, $p_{(wt\ to\ +/-)}$=0.11 and $p_{(+/-\ to\ -/-)}$=0.14). Western blot analysis confirmed that similar levels of the GP Ib and GP IX were also present in platelet lysates from all three genotypes.

Figure 6:
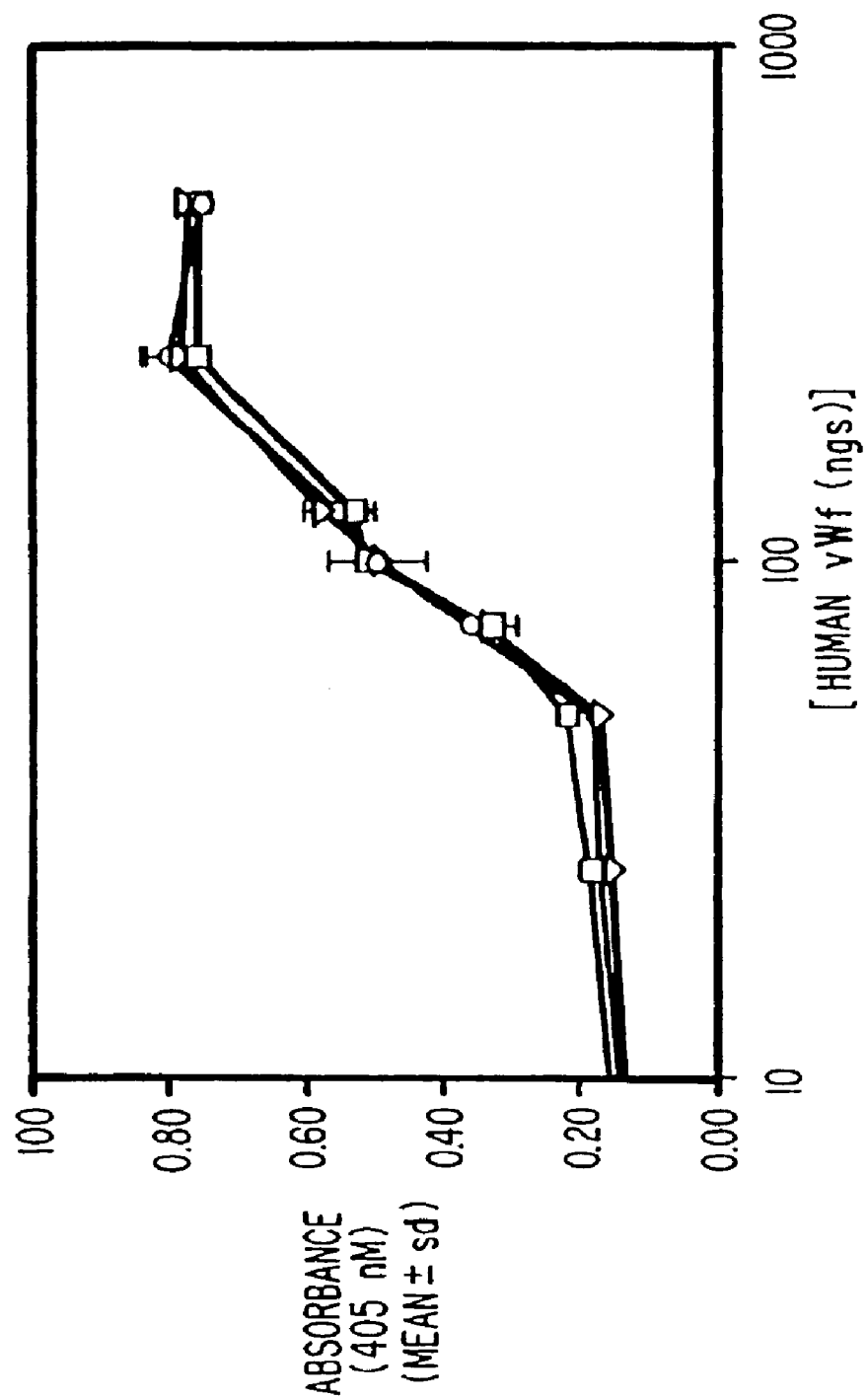
FIG. 6 shows binding of GP V −/− platelets to immobilized human vWf. Pooled WP from wt (□), +/− (V) and −/− (○) mice were incubated as described in Methods. The data shown is the average of duplicates and is representative of 3 such experiments.
Figure 7:
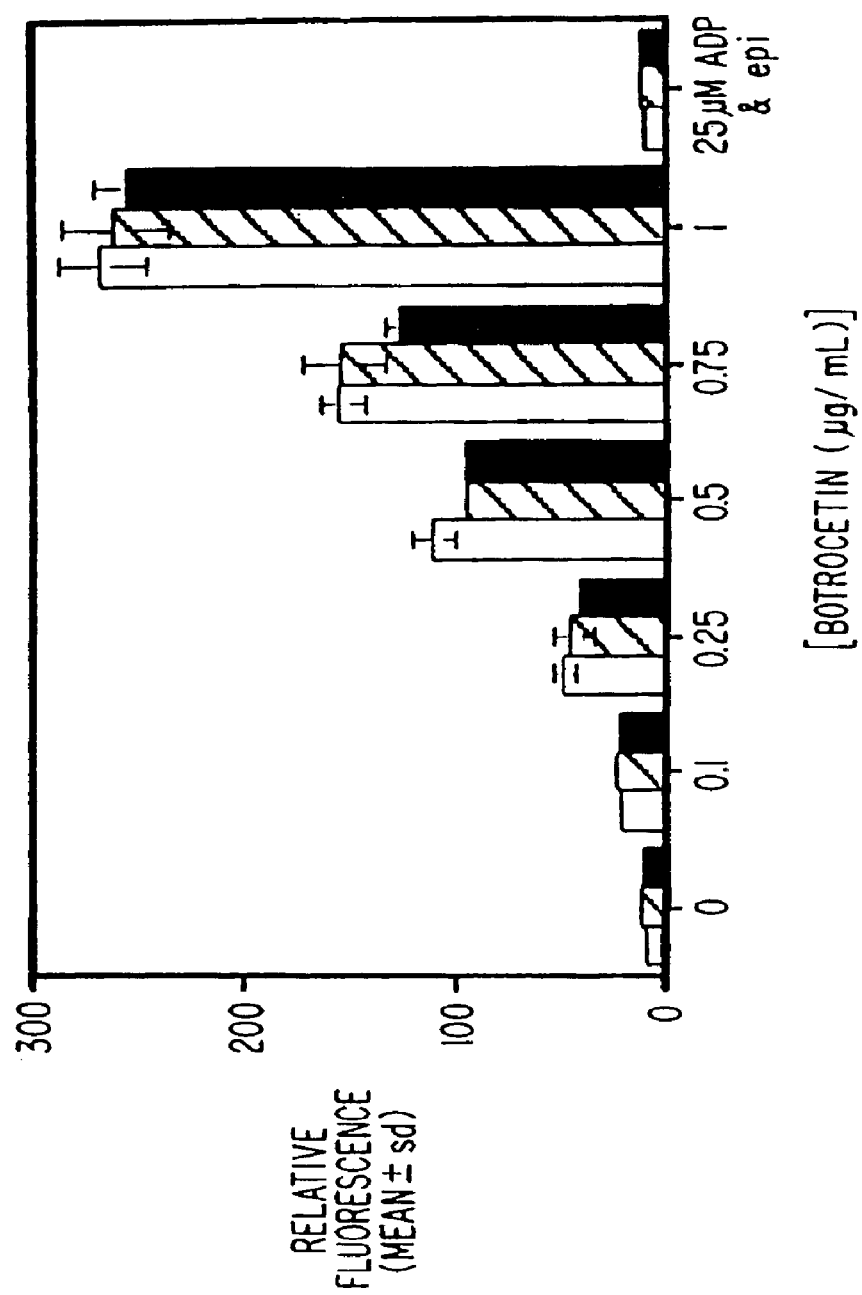
FIG. 7 shows binding of FITC~vWf to GP V−/− platelets. Pooled PRP from GP V wt (□), +/− (dashed) and −/− (■) mice were incubated with FITC~vWf and botrocetin and analyzed by flow cytometry. The data is representative of 3 experiments done in duplicate.

Two assays were used to determine whether the GP Ib expressed on GP V −/− platelets was functional. One assay measured the adhesion of platelets to immobilized vWf that was activated by botrocetin to bind GP Ib. FIG. 6 shows that GP V −/− platelets bound to immobilized, botrocetin-activated human vWf in a manner indistinguishable from wt platelets. Under these conditions, the binding of vWf to platelets is mediated entirely by GP Ib, since purified human glycocalicin (a soluble, extracellular fragment of GP Ibα that contains the vWf binding domain), inhibited botrocetin-induced binding of platelets to vWf in a concentration-dependent manner (not shown). We also found that soluble, activated vWf bound identically to platelets from all three genotypes in PRP (FIG. 7). Again, botrocetin-induced vWf binding could be completely inhibited by purified human glycocalicin (not shown). Furthermore, stimulation of αIIbβ3 on platelets by ADP and epinephrine did not induce soluble vWf binding (FIG. 7). Thus GP Ib-IX expressed in the GP V−/− platelets was functional.

Example 5

Effect of GP V Gene Deletion on Thrombin-Induced Platelet Function

Figure 8:
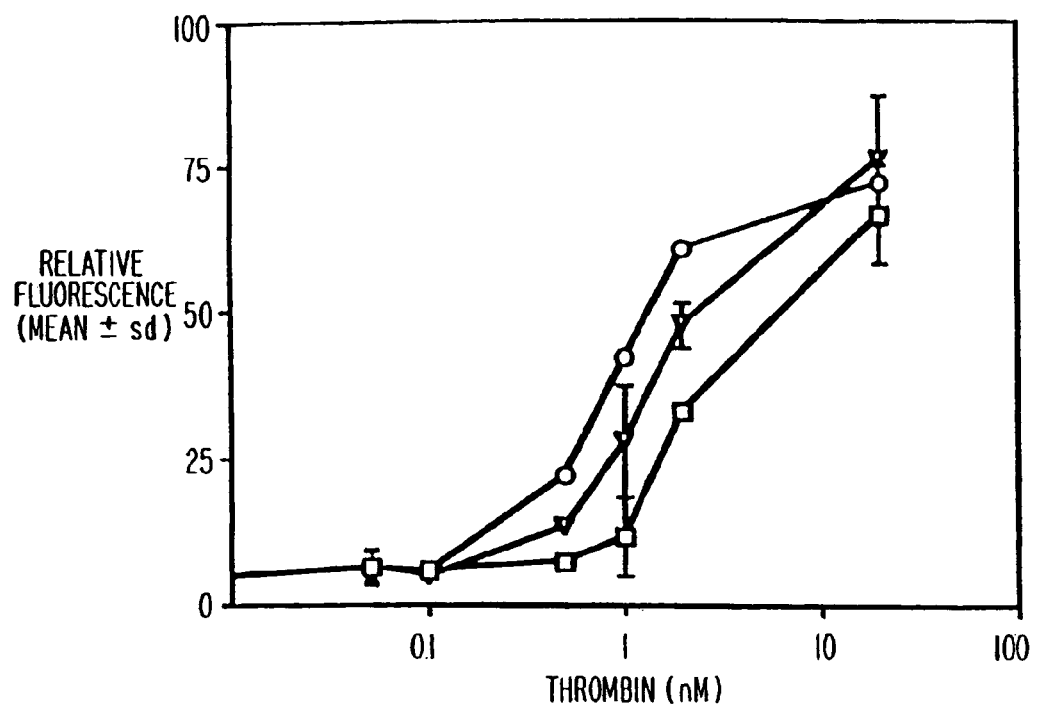
FIG. 8 shows thrombin-induced FITC~fibrinogen binding in washed platelets from GP V wt, +/− and −/− mice. Mouse WP from individual mice [wt (□) +/− (V) and −/− (○)] were stimulated with the indicated amounts of thrombin. The platelets were incubated with FITC~labeled fibrinogen for 30 min fixed and analyzed by flow cytometry. The data is representative of 3 experiments done in duplicate.

As shown in FIG. 8, thrombin at low concentrations (0.5 nM) induced significantly increased binding of FITC-fibrinogen in GP V −/− platelets compared to wt (Mean RFU±sd wt=7±1.2, +/−=13.2±0.9 and −/−=22±0.8). This difference persisted at 1 nM thrombin (Mean RFU±sd wt=11.5±6.8, +/−=27.9±9.45 and −/−=42±1.8). However, platelets from all genotypes were able to bind FITC-fibrinogen equivalently at high (20 nM) thrombin concentrations (Mean RFU±sd wt=66.5±8.6, +/−=76.1±11.3 and −/−=72±0.2). The apparent $EC_{50}$ values for thrombin were approximately 2 nM for wt platelets and 0.7 nM for the −/− platelets. P-Selectin expression was also greater in the GP V−/− platelets at low thrombin concentrations, compared to wt (not shown).

Consistent with the FITC-fibrinogen results, platelets lacking GP V exhibited an increased aggregation response to thrombin compared to wt platelets. Indeed, platelets from GP V −/− mice aggregated when treated with sub-threshold concentrations of thrombin (0.5 nM) that did not induce a significant response in wt platelets (FIG. 9).

As observed in the fibrinogen binding studies, platelets from GP V+/− heterozygous animals gave an intermediate response in the aggregation assays. We determined if this increased responsiveness was related to increased expression of $\alpha IIb\beta 3$, using an antibody specific for the mouse fibrinogen receptor. The levels of $\alpha IIb\beta 3$ were comparable on platelets from animals of all three genotypes by flow cytometry (Mean RFU wt=1554±386; +/−=1246±202; and −/−=1435±77; $p_{(wt\ to\ -/-)}=0.65$, $p_{(wt\ to\ +/-)}=0.31$ and $p_{(+/-\ to\ -/-)}=0.24$), and were also similar by Western blotting.

Example 6

Determination of Bleeding Time

To determine the consequences of enhanced platelet function in GP V −/− mice, bleeding time measurements were performed using a tail cut model, which was previously shown to be platelet dependent (Hodivala-Dilke, K. M., McHugh, K. P., Tsakiris, D. A., Rayburn, H., Crowley, D., Ullman-Cullere, M., Ross, F. P., Coller, B. S., Teitelbaum, S. & Hynes, R. O. (1999) *J Clin Invest* 103, 229–38; Tsakiris, D. A., Scudder, L., Hodivala-Dilke, K, Hynes, R. O. & Coller, B. S. (1999) *Thrombosis and Haemostasis* 81, 177–188).

Consistent with the in vitro data, GP V −/− mice had a statistically shorter bleeding time (Mean±sem=178±21 sec) than wt littermate control mice (276±35 sec, Student's T-test p=0.016). The bleeding time in the +/− animals was intermediate (224±25 sec) but not statistically different from either wt or −/− mice. Furthermore, 70% of the −/− mice had bleeding times less than 120 sec, compared to 50% of the wt and +/− mice. Conversely, 21.6% of the wt mice had bleeding times greater than 500 sec, compared to 9.5% in the +/− mice and 8.5% in the −/− mice. The difference in bleeding time is also statistically significant using nonparametric analysis (Mann-Whitney test p=0.046). Thus the increased aggregability of the platelets from GP V−/− mice observed in in vitro assays translates into a shorter bleeding time in vivo.

Example 7

Additional Examples

As explained herein, the mice produced according to this invention are useful in addressing the role of GP V, which is part of a complex on the platelet surface that is critical for high shear (arterial) platelet adhesion. Preliminary examination of platelets from these mice has already dispelled the hypothesis that GP V is required for the expression of the complex on the platelet surface, since animals deficient in the GP V gene express the remainder of the complex (subunits GPIb-IX) at levels grossly equivalent to the platelets of wild type animals as determined by flow cytometry.

Based on this information, GP V may have several biological functions. These include the following.

1. Role in platelet activation by thrombin.

a) Cleavage of GP V by thrombin may be essential for the activation of the platelet by the subsequent generation of an intracellular signal which results in the inside-out activation of GPIIb-IIIa If cleavage is essential mice in which GP V is absent from the platelet surface would have a severe bleeding diathesis similar to that observed in Bernard-Soulier patients.

b) GP V may function analogous to a brake with cleavage of GP V allowing platelet activation via signaling through the GPIb-IX complex, and inside out activation of GPIIb-IIIa. Platelets which are deficient or lacking in GP V would be proaggregable. Thus platelets from GP V deficient mice may show a predilection to aggregation and a tendency to aggregate more quickly than wild type mouse platelets.

2. Role in coagulation. The kinetics of GP V cleavage reveals that GP V is cleaved at very low thrombin concentrations and suggests a possible role for GP V cleavage as part of the cascade of reactions that occurs during coagulation. While it is believed that platelet surfaces contribute to the rapid generation of thrombin which is the end product of the coagulation cascade, the various proteins on platelets which may be involved have not yet been identified. Since the cleavage of GP V occurs at concentrations of thrombin much lower than that required to cleave other platelet surface proteins, GP V cleavage may be part of the process which occurs in arteries which culminates in the formation of a thrombus.

Activators of GP V cleavage may have a prothrombotic effect. Prevention of GP V cleavage may be a viable means of preventing arterial thrombosis especially under high shear conditions. Accordingly, inhibitors of GP V cleavage may be useful as drugs to prevent the clinical consequences of platelet activation like unstable angina and myocardial infarction.

The availability of mice, genetically lacking GP V will allow for the testing of these GP V functions. Platelets from these mice can be used in a variety of assays such as aggregation, agglutination, fibrinogen binding in response to a number of platelet agonists like thrombin, ADP, thromboxane A2, collagen etc. in order to characterize the effect of loss of GP V on the functional response of these platelets.

In addition the mice of Example 1 provide useful in vivo animal models of haemostasis and thrombosis which will allow for the determination of the role of GP V in such processes and, should provide a specific model to study GP V as a therapeutic target.

Although the present invention has been described in detail with reference to examples above, it is understood that various modifications can be made without departing from the spirit of the invention. Accordingly, the invention is limited only by the following claims. All cited patents, applications and publications referred to in the application are hereby incorporated by reference in their entirety.

What is claimed:

1. A transgenic mouse comprising a modified glycoprotein V (GP V) gene, wherein the mouse is genome has a homozygous modification with a construct which removes a sequence of GP V gene comprising nucleotides encoding Met 1 to Leu 389 of SEQ ID NQ:12 and wherein said mouse has platelets with an increased aggregation response to a low concentration of thrombin compared to platelets from a mouse homozygous for the wild type GP V gene.

2. Platelets isolated from blood plasma of the mouse of claim 1.

3. A method of preparing a transgenic mouse comprising a modified glycoprotein V gene, wherein the mouse is genome has a homozygous modification with a construct which removes a sequence of GP V gene comprising nucleotides encoding Met 1 to Leu 389 of SEQ ID NO:12, said method comprising:
    a) introducing into embryonic stem cells a nucleic acid molecule a comprising a construct which removes a sequence of GP V gene comprising nucleotides encoding Met 1 to Leu 389 of SEQ ID NO:12;
    b) generating a transgenic mouse from the cells resulting from step a);
    c) breeding the transgenic mouse to obtain a transgenic mouse homozygous for the modified GP V gene; and
    d) determining that platelets from the homozygotic transgenic mouse have an increased aggregation response to a low concentration of thrombin compared to platelets from a mouse homozygous for the GP V gene.

4. A method of preparing a transgenic mouse is genome comprising a nonfunctional glycoprotein V gene, wherein the mouse has a homozygous modification with a construct which removes a sequence of GP V gene comprising nucleotides encoding Met 1 to Leu 389 of SEQ ID NO:12, said method comprising:
    a) introducing into embryonic stem cells a nucleic acid molecule comprising a construct which removes a sequence of GP V gene comprising nucleotides encoding Met 1 to Leu 389 of SEQ ID NO:12 and a selectable marker;
    b) identifying and selecting transformed cells;
    c) injecting the transformed cells from step b) into blastocysts;
    d) generating a transgenic mouse from the blastocysts of step c), wherein the generated transgenic mouse is chimeric for the nonfunctional GP V gene and wherein said mouse has platelets with an increased aggregation response to a low concentration of thrombin compared to platelets from a mouse homozygous for the wild type GP V gene;
    e) breeding the chimeric mouse with a wild-type mouse to produce a mouse heterozygotic for the nonfunctional GP V gene;
    f) crossing a heterozygotic mouse produced in step e) with a mouse which is chimeric or heterozygotic for the nonfunctional GP V gene; and
    g) selecting a mouse homozygotic for the nonfunctional GP V gene from the resulting progeny.

5. A method to identify an agent that modulates a thrombotic response of a transgenic mouse whose genome has a modified GP V gene, wherein the mouse is genome has a homozygous modification with a construct which removes a sequence of GP V gene comprising nucleotides encoding Met 1 to Leu 389 of SEQ ID NO:12 and wherein said mouse has platelets with an increased aggregation response to a low concentration of thrombin compared to platelets from a mouse homozygous for the wild type GP V gene, comprising the step of exposing the mouse to the agent and determining whether the agent modulates the thrombotic response.

6. A method of determining the effect of an agent on a characteristic of a mouse that is attributable to the expression of the GP V gene, wherein the mouse is genome has a homozygous modification with a construct which removes a sequence of GP V gene comprising nucleotides encoding Met 1 to Leu 389 of SEQ ID NO:12 and wherein said mouse has platelets with an increased aggregation response to a low concentration of thrombin compared to platelets from a mouse homozygous for the wild type GP V gene, and wherein said characteristic is platelet function, said method comprising;
    a) administering said agent to the mouse of claim 1;
    b) maintaining said mouse for a desired period of time after said administration; and,
    c) determining whether the characteristic of said mouse that is attributable to the expression of the modified GP V gene has been affected by the administration of said agent.

7. A cell isolated from a transgenic mouse that comprises a transgene stably integrated into the mouse's genome, said transgene encoding a modified glycoprotein V gene, wherein the mouse is genome has a homozygous modification with a construct which removes a sequence of GP V gene comprising nucleotides encoding Met 1 to Leu 389 of SEQ ID NO:12 and wherein said mouse has platelets with an increased aggregation response to a low concentration of thrombin compared to platelets from a mouse homozygous for the wild type GP V gene.

8. The mouse of claim 1, wherein said mouse is fertile and transmits the modified GP V gene to its offspring.

9. A method of determining the effect of an agent on a characteristic of a mouse that is attributable to the expression of the GP V gene, wherein the mouse is genome has a homozygous modification with a construct which removes a sequence of GP V gene comprising nucleotides encoding Met 1 to Leu 389 of SEQ ID NQ:12 and wherein said mouse has platelets with an increased aggregation response to a low concentration of thrombin compared to platelets from a mouse homozygous for the wild type GP V gene, and wherein said characteristic is hemostasis, said method comprising;
    a) administering said agent to the mouse of claim 1;
    b) maintaining said mouse for a desired period of time after said administration; and,
    c) determining whether the characteristic of said mouse that is attributable to the expression of the modified GP V gene has been affected by the administration of said agent.

10. A method of determining the effect of an agent on a characteristic of a mouse that is attributable to the expression of the GP V gene, wherein the mouse is genome has a homozygous modification with a construct which removes a sequence of GP V gene comprising nucleotides encoding Met 1 to Leu 389 of SEQ ID NO:12 and wherein said mouse has platelets with an increased aggregation response to a low concentration of thrombin compared to platelets from a mouse homozygous for the wild type GP V gene, and wherein said characteristic is coagulation, said method comprising;
    a) administering said agent to the mouse of claim 1;
    b) maintaining said mouse for a desired period of time after said administration; and, c) determining whether the characteristic of said mouse that is attributable to the expression of the modified GP V gene has been affected by the administration of said agent.

11. A method of determining the effect of an agent on a characteristic of a mouse that is attributable to the expression of the GP V gene, wherein the mouse is genome has a homozygous modification with a construct which removes a sequence of GP V gene comprising nucleotides encoding Met 1 to Leu 389 of SEQ ID NO:12 and wherein said mouse has platelets with an increased aggregation response to a low concentration of thrombin compared to platelets from a mouse homozygous for the wild type GP V gene, and wherein said characteristic is thrombosis, said method comprising;

a) administering said agent to the mouse of claim 1;

b) maintaining said mouse for a desired period of time after said administration; and, c) determining whether the characteristic of said mouse that is attributable to the expression of the modified GP V gene has been affected by the administration of said agent.

* * * * *